US008080428B2

(12) United States Patent
Beuerman et al.

(10) Patent No.: US 8,080,428 B2
(45) Date of Patent: Dec. 20, 2011

(54) INVESTIGATION OF MUCOSA DRYNESS CONDITIONS

(75) Inventors: Roger Beuerman, Singapore (SG); Lei Zhou, Singapore (SG); Shouping Liu, Singapore (SG); He Yang, Singapore (SG); Donald Tan, Singapore (SG)

(73) Assignees: Singapore Health Services Pte Ltd., Singapore (SG); Agency for Science, Technology and Research, Singapore (SG)

( * ) Notice: Subject to any disclaimer, the term of this patent is extended or adjusted under 35 U.S.C. 154(b) by 229 days.

(21) Appl. No.: 12/298,829

(22) PCT Filed: Apr. 26, 2007

(86) PCT No.: PCT/SG2007/000118
§ 371 (c)(1),
(2), (4) Date: Oct. 28, 2008

(87) PCT Pub. No.: WO2007/126391
PCT Pub. Date: Nov. 8, 2007

(65) Prior Publication Data
US 2009/0258828 A1 Oct. 15, 2009

Related U.S. Application Data

(60) Provisional application No. 60/795,676, filed on Apr. 28, 2006.

(51) Int. Cl.
*A61K 49/00* (2006.01)
*A61K 49/14* (2006.01)
*G01N 24/00* (2006.01)
*C12Q 1/00* (2006.01)
*G01N 33/53* (2006.01)
*C07K 2/00* (2006.01)
*C07K 14/435* (2006.01)

(52) U.S. Cl. ............. 436/173; 424/9.1; 424/811; 435/4; 530/350

(58) Field of Classification Search ...................... None
See application file for complete search history.

(56) References Cited

U.S. PATENT DOCUMENTS
2006/0051744 A1 3/2006 Austin et al.

FOREIGN PATENT DOCUMENTS
| DE | 10017249 A1 | 10/2001 |
| WO | 02/077176 A2 | 10/2002 |
| WO | 2004/081033 A2 | 9/2004 |
| WO | 2007/057746 A2 | 5/2007 |

OTHER PUBLICATIONS

Abe et al., Br J Ophthalmol. 1999; 83: 684-687.*
Nakanishi, J. Electrophoresis, 2004; 48: 99-103; article in Japanese.*
Translation of Nakanishi, J. Electrophoresis, 2004; 48: 99-103 (reference U); 15 pages total.*
Mackie, I. A. et al. "Confirmatory tests for the dry eye of Sjogren's Syndrome". Scandanavian Journal of Rheumatology, 1986, Suppl. 61, p. 220-223.
Deluise, V.P. et al. "Quantitation of tear lysozyme levels in dry-eye disorders". Archives of Ophthalmology, 1983, vol. 101, No. 4, p. 634-635.
Grus, F. H., et al. "SELDI-TOF-MS Protein Chip array profiling of tears from patients with dry eye". Investigative Ophthalmology and Visual Science, 2005, vol. 46, No. 3, p. 863-876.
Da Dalt, S. et al. "The lactoferrin tear test in the diagnosis of Sjogren's Syndrome". European Journal of Ophthalmology, 1996, vol. 6, No. 3, p. 284-286.
Mackie, A. et al. "Diagnostic implications of tear protein profiles". British Journal of Ophthalmology, 1984, vol. 68, No. 5, p. 321-324.
Hu, F. R. "Tear lactoferrin in keratoconjunctivitis sicca". Taiwan yi xue hui za zhi. Journal of the Formosan Medical Association, 1989, vol. 88, No. 4, p. 422-425.
Boersma, H.G. et al. "The lactoferrin test for the diagnosis of keratoconjunctivitis sicca in clinical practice". Annals of Ophthalmology, 1987, vol. 19, p. 152-154.
Dogru, et al., "New Insight into the Diagnosis and Treatment of Dry Eye," The Ocular Surface, vol. 2, No. 2, Apr. 2004, pp. 59-75.
Sullivan, David A., "Tearful Relationships? Sex, Hormones, the Lacrimal Gland, and Aqueous-Deficient Dry Eye," The Ocular Surface, vol. 2, No. 2, Apr. 2004, pp. 92-123.
Schein, et al., "Prevalence of Dry Eye Among the Elderly," American Journal of Ophthalmology, vol. 124, No. 6, 1997, pp. 723-728.
Lemp, Michael A., "Report of the National Eye Institute/Industry Workshop on Clinical Trials in Dry Eyes," The CLAO Journal, vol. 21, No. 4, Oct. 1995, pp. 221-232.
Ousler, et al., "Methodologies for the Study of Ocular Surface Disease," The Ocular Surface, vol. 3, No. 3, Jul. 2005, pp. 143-154.
Ross, et al., "Multiplexed Protein Quantitation in *Saccharomyces cerevisiae* Using Amine-Reactive Isobaric Tagging Reagents," Molecular & Cellular Proteomics, vol. 3, 2004, pp. 1154-1169.
Pancholi, V., "Multifunctional α-enolase: its role in disease," Cell. Mol. Life Sci., vol. 58, 2001, pp. 902-920.
Hochepied, et. al, "$\alpha_1$ -Acid Glycoprotein: An Acute Phase Protein with Inflammatory and Immounomodulating Properties," Cytokine & Growth Factor Reviews, vol. 14, 2003, pp. 25-34.
Roth, et al., "Phagocyte-Specific S100 Proteins: A Novel Group of Proinflammatory Molecules," Trends in Immunology, vol. 24, No. 4, Apr. 2003, pp. 155-158.
Grus, et al., "SELDI-TOF-MOS ProteinChip Array Profiling of Tears from Patients With Dry Eye," Investigative Ophthalmology & Visual Science, vol. 46, No. 3, Mar. 2005, pp. 863-876.

(Continued)

*Primary Examiner* — Bridget E Bunner
*Assistant Examiner* — Christina Borgeest
(74) *Attorney, Agent, or Firm* — Heslin Rothenberg Farley & Mesiti P.C.; Andrew K. Gonsalves

(57) ABSTRACT

The present invention relates to diagnosis and/or treatment of medical conditions. The present invention relates to new method of diagnosing dry mucosa condition in a subject. The condition may be dry eye. The present invention also provides a method to monitor the efficacy of a treatment of a dry mucosa condition, a method of treating a dry mucosa condition and/or a diagnostic kit for a dry mucosa condition.

8 Claims, 25 Drawing Sheets

OTHER PUBLICATIONS

Ryan, et al., "Involvement of S100A4 in Stromal Fibroblasts of the Regenerating Cornea," Investigative Ophthalmology & Visual Science, vol. 44, No. 10, Oct. 2003, pp. 4255-4262.

Sherbet, et al., "S100A4 (MTS1) Calcium Binding Protein in Cancer Growth, Invasion and Metastasis," Anticancer Research, vol. 18, 1998, pp. 2415-2422.

Kanamori, et al., "Increased Expression of Calcium-Binding Protein S100 in Human Uterine Smooth Muscle Tumors," Molecular Human Reproduction, vol. 10, No. 10, Aug. 20, 2004, pp. 735-742.

Ohashi, et al., "Abnormal Protein Profiles in Tears With Dry Eye Syndrome," Am. J. Ophthamol., 2003, pp. 291-299.

Redl, Bernard, "Human Tear Lipocalin," Biochimica et Biophysica Acta, vol. 1482, 2000, pp. 241-248.

Clark, et al., "The Potential Role for Prolactin-Inducible Protein (PIP) as a Marker of Human Breast Cancer Micrometastasis," British Journal of Cancer, vol. 81, No. 6, 1999, pp. 1002-1008.

Koo, et al., "Comparative Analysis of the Tear Protein Expression in Blepharitis Patients Using Two-Dimensional Electrophoresis," Journal of Proteome Research, vol. 4, No. 3, 2005, pp. 719-724.

Zhou et al., "Characterisation of Human Tear Proteins Using High-Resolution Mass Spectrometry,"Annals Academy of Medicine Singapore, vol. 35, No. 6, Jun. 2006, pp. 400-407.

Dickinson, et al., "A Major Human Lacrimal Gland mRNA Encodes a New Proline-Rich Protein Family Member," Investigative Ophthalmology & Visual Science, vol. 36, No. 10, Sep. 1995, pp. 2020-2031.

Thomas, Robert, "Recent Developments in LC-MS-MS for the Identification and Measurement of Nanoscale Amounts of Proteins and Peptides," Spectroscopy, vol. 16, No. 1, 2001, pp. 28-37.

Wold, et al., "Studies on the Enzyme Enolase. I. Equilibrium Studies," J. Biol. Chem., vol. 227, Jul. 1957, pp. 301-312.

Dietrich, et al., "Nanoarrays: A Method for Performing Enzymatic Assays," Analytical Chemistry, vol. 76, No. 14, 2004, pp. 4112-4117.

Supplemental European Search Report issued in EP07748663, search completed Sep. 21, 2010.

Zhou et al., "Identification of tear fluid biomarkers in dry eye syndrome using iTRAQ quantitative proteomics," *Journal of Proteome Research*, 8(11):4889-4905 (2009).

\* cited by examiner

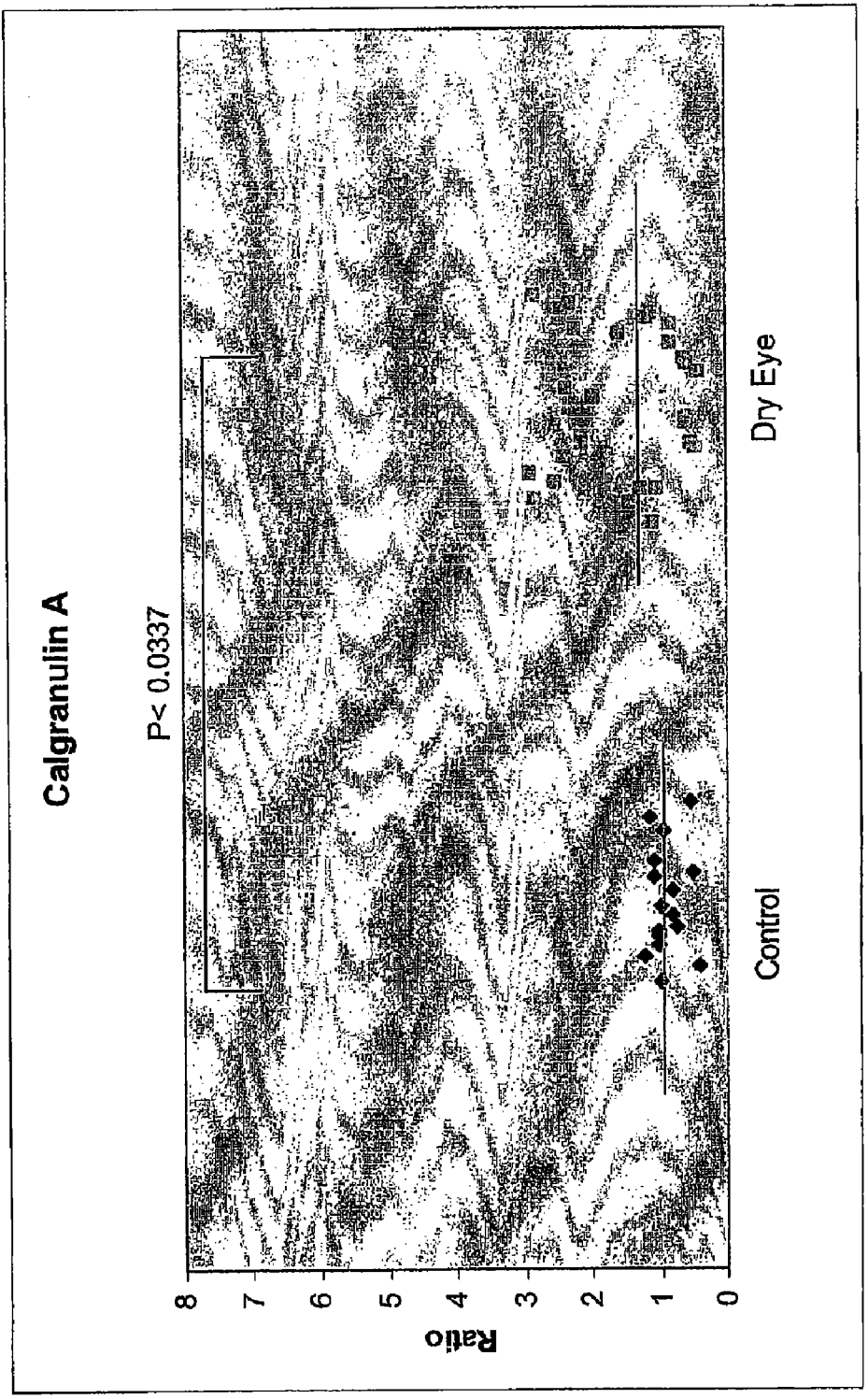

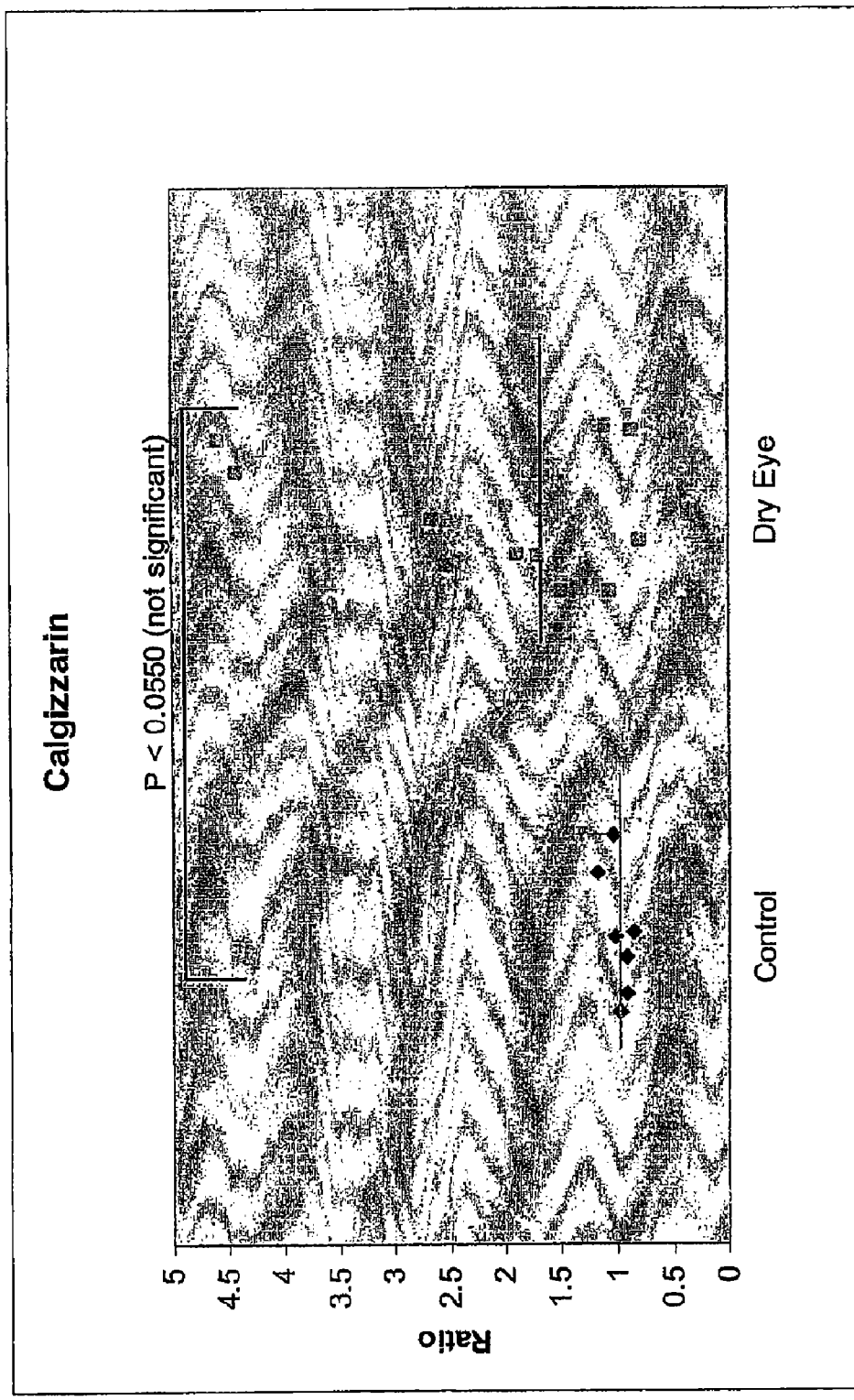

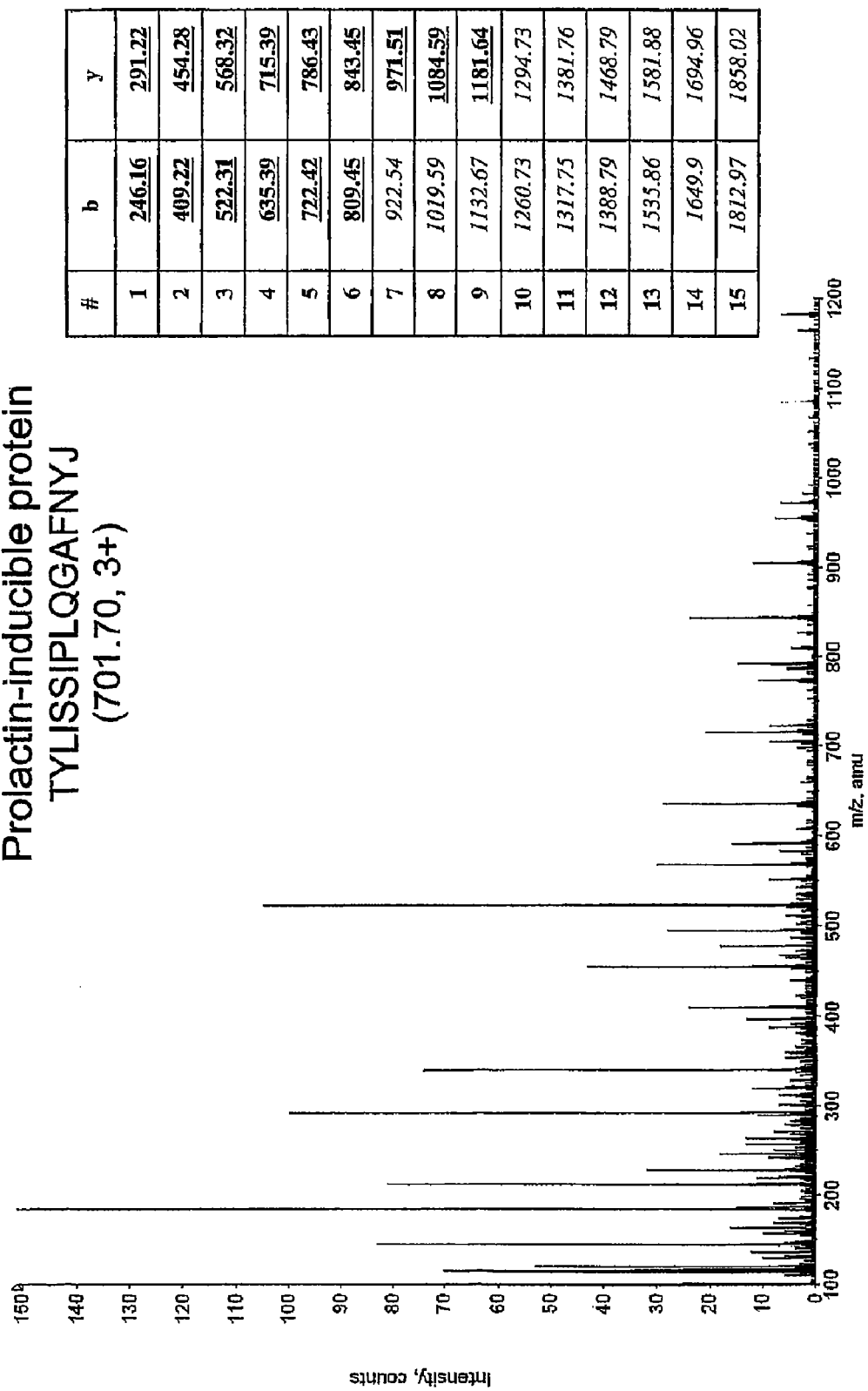

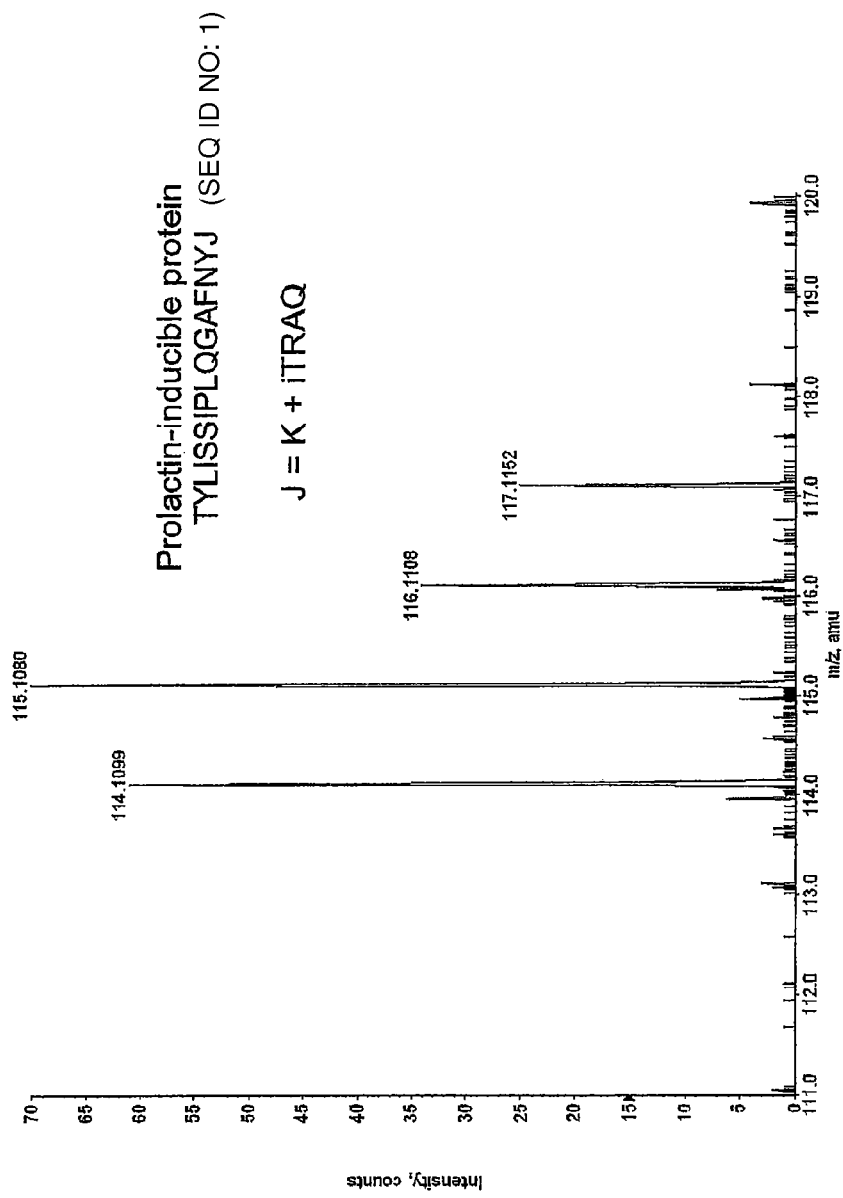

Alpha-enolase
SGETEDTFIADLVVGLCTGQIJ
(877.40, 3+)
(SEQ ID NO: 2)

Alpha-1-acid glycoprotein 1
YVGGQEHFAHLLILR
(475.00, 4+)
(SEQ ID NO: 3)

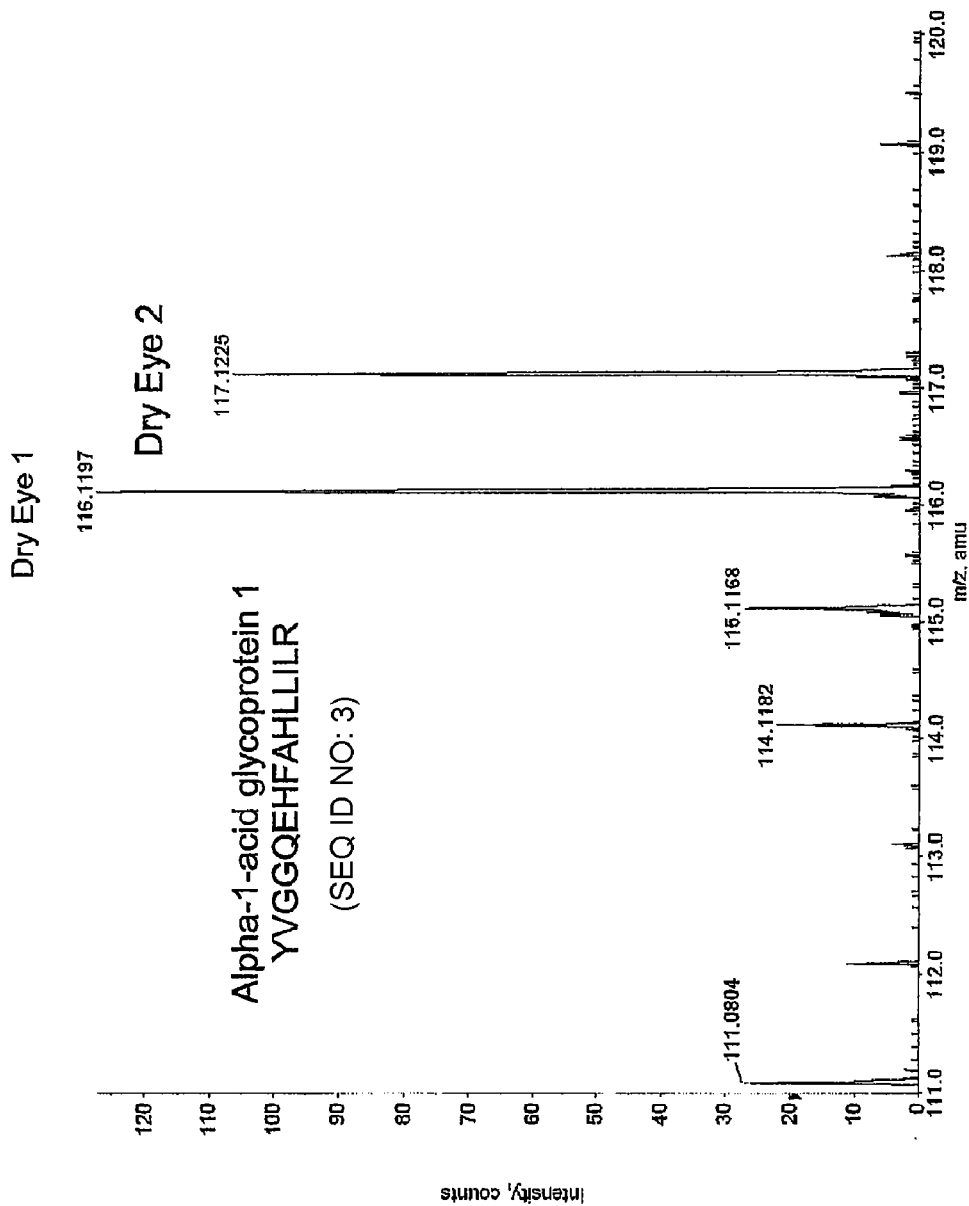

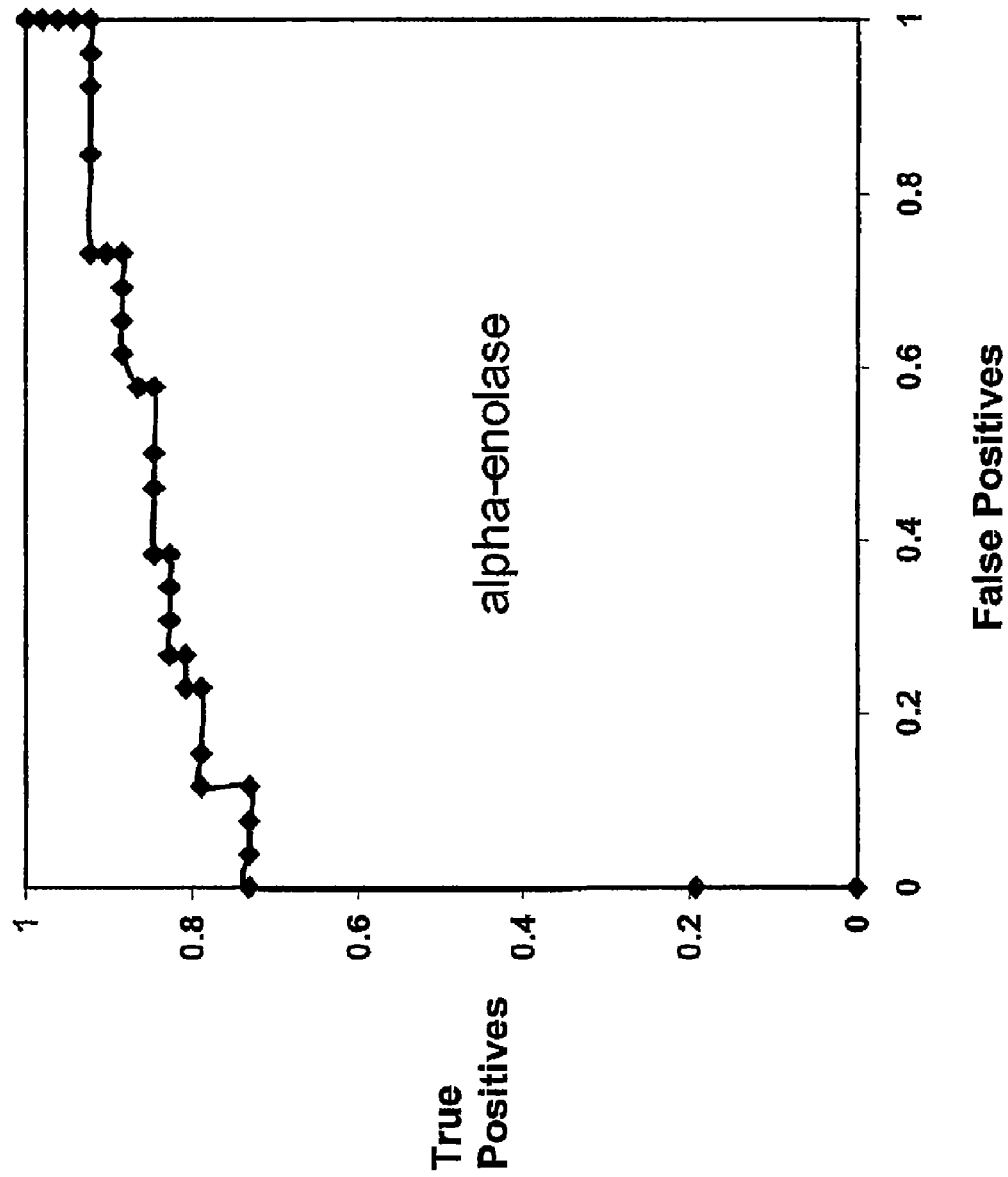

INVESTIGATION OF MUCOSA DRYNESS CONDITIONS

CROSS REFERENCE TO RELATED APPLICATIONS

This application is a U.S. National Phase filing under 35 U.S.C. §371 of International Application PCT/SG2007/000118, filed Apr. 26, 2007, and published as WO 2007/126391 on Nov. 8, 2007. PCT/SG2007/000118 claimed benefit of priority from U.S. Provisional Application No. 60/795,676, filed Apr. 28, 2006. The entire contents of each of the prior applications are incorporated herein by reference.

FIELD OF THE INVENTION

The present invention relates to medical conditions. In particular, the present invention relates to mucosa dryness conditions.

BACKGROUND OF THE INVENTION

Sjogren Syndrome is an autoimmune inflammatory disease characterized by a particular form of dry mouth and dry eyes. It affects the lacrimal gland's ability to secrete tears and results in dry eye, salivary gland dysfunction, causing dry mouth and dryness in other mucous membranes such as the bronchial epithelium, the vagina and other mucosa.

This loss of tear and saliva fluids may result in characteristic changes in the eyes (called aqueous tear deficiency or keratoconjunctivitis sicca) and in the mouth with deterioration of the teeth, increased oral infection, difficulty in swallowing, and painful mouth. However, dry mucosa may also be due to other causes classified under the non-Sjogren Syndrome. The causes may be due to use of certain types of drugs, inflammation or infection, or hypothyroidism. Dry mucosa conditions due to any cause can affect both humans and animals such as mammals.

For the eyes, the lacrimal gland located in the orbit of the eye continuously secretes small amounts of tear fluid that are released onto the surface of the eye through very small ducts. Dry eye syndrome can be defined as a loss of tear fluid with accompanying abnormalities of the tear film. There are few objective signs of dry eye and importantly, discomfort which varies on an individual basis is the aspect that is most noticed by patients and which motivates them to seek help [1]. For severe cases, ocular surface damage and a loss of vision is not uncommon. Dry eye syndrome affects millions of people and its prevalence is estimated to be as high as 11~22% of the general population with the prevalence in Asia greater than in the West [1]. It is more common in people over 55 years of age and in females; however, in Asia, dry eye is a factor in those over 45 [2]. The prevalence is also significantly higher in visual display terminal users and contact lens wearers.

The causes for dry eye syndrome are diverse; however, fundamentally it is due to a loss of fluid over the ocular surface and particularly the cornea. The cornea is the most important optical element of the eye and dry eye decreases good vision as well as the quality of life of the patient. The fluid layer over the ocular surface, called the tear layer, is some microns thick but has layers as follows: 1-outermost lipid layer, 2-middle aqueous layer and 3-inner mucin layer. Usually it can be classified into two major categories: tear secretion deficiency and excessive tear evaporation. Dysfunction of the lipid layer of the tear film leads to excessive evaporation of tears. A mucin layer deficiency often caused by vitamin A deficiency; however, except for developing countries, it is rare.

For therapeutic development by pharmaceutical companies for dry eye, non-Sjogren's dry eye is the primary target as it comprises the majority of these patients. At present there is only one actual therapeutic drug on the market, Restasis® from Allergan®. The reasons for this paucity in drug development arise primarily from the lack of objective measures of dry eye and therapeutic efficacy.

Diagnosis of dry eye syndrome is typically based on subjective symptoms, Schirmer test (evaluating quantity of tear fluid), tear break-up time (evaluating quality of tear film) and other less common clinical tests including fluorescein staining, Rose Bengal staining, measuring tear meniscus height, impression cytology, and others. Studies show that correlation is poor between clinical tests and symptoms and even between different clinical tests [3, 4]. This also makes a difficult scenario for the evaluation of therapeutic agents [5].

As such, new and improved methods of determining and diagnosing dry mucosa conditions such as dry eye are welcome.

SUMMARY OF THE INVENTION

The present invention addresses the problems above, and in particular, provides methods for diagnosis and treatment of a medical condition. In general, the present invention provides new method to diagnose dry mucosa condition in a subject.

In one aspect, the present invention relates to a method of diagnosing a dry mucosa condition in a subject, the method comprising: providing a sample from the subject; and comparing expression of at least one biomarker in the sample, the at least one biomarker selected from the group consisting of α-enolase, α-1-acid-glycoprotein, prolactin-inducible protein, S100 A8, S100 A9, S100 A4, S100 A11, von Ebner's gland protein, lactoferrin, lysozyme, proline-rich 4 protein, and any of their derivative or fragment thereof with at least one reference value.

In another aspect, the present invention provides a method of determining the severity of the condition of dry mucosa in a subject, the method comprising: providing a sample from the subject; and comparing the relative expression of α-1-acid-glycoprotein, S100 A8, S100 A9, S100 A4, S100 A11, lactoferrin, lysozyme, and/or any of their derivative or fragment thereof in the sample with at least one reference value.

In another aspect, the present invention provides a method of monitoring efficacy of a treatment for a dry mucosa condition in a subject, the method comprising: providing a sample from the subject; and comparing expression of at least one biomarker in the sample, the at least one biomarker selected from the group consisting of α-enolase, α-1-acid-glycoprotein, prolactin-inducible protein, S100 A8, S100 A9, S100 A4, S100 A11, von Ebner's gland protein, lactoferrin, lysozyme, proline-rich 4 protein and any of their derivative or fragment thereof with at least one reference value.

In another aspect, the present invention provides a method of treating a dry mucosa condition in a subject, the method comprising: providing a sample from the subject; comparing expression of at least one biomarker in the sample, the at least one biomarker selected from the group consisting of α-enolase, α-1-acid-glycoprotein and prolactin-inducible protein, S100 A8, S100 A9, S100 A4, S100 A11, von Ebner's gland protein, lactoferrin, lysozyme, proline-rich 4 protein and any of their derivative or fragment thereof; and reducing the difference in expression of at least one biomarker in the group of biomarkers.

In the above aspects, the dry mucosa condition may be dry eye. The comparing may be with at least one reference value determined from at least one subject not exhibiting signs of, or experiencing symptoms of the dry mucosa condition, and/or the comparing may be with at least one reference value determined from a statistically significant number of subjects not exhibiting signs of, or experiencing symptoms of the dry mucosa condition. The sample may be a fluid. The expression of the biomarker may be reflected in, or measured by the abundance of the at least one biomarker. The comparing may be by mass spectrometry. The subject may be a human being or a mammal.

Under the method for treating a dry mucosa condition, the at least one biomarker may be α-1-acid-glycoprotein 1 and the reducing of the difference in expression comprises reducing inflammation in the subject. The at least one biomarker may be prolactin-inducible protein and the reducing of the difference in expression comprises increasing the expression of prolactin-inducible protein in the subject by the administration of prolactin and/or androgen. The at least one biomarker may be S100 A8 and S100 A9 and the reducing of the difference in expression comprises reducing the upregulation and/or complex formation, of S100 A8 and S100 A9 in the subject.

In another aspect, the present invention provides a panel of biomarkers for diagnosing the condition of dry eye, the panel comprising α-enolase, prolactin-inducible protein, α-1-acid-glycoprotein, S100 A8, S100 A9, S100 A4, S100 A11, lactoferrin, lysozyme, von Ebner's gland protein, proline-rich 4 protein, and/or a derivative or fragment thereof with at least one reference value. The panel may provide a more detailed profile of the condition, yielding both diagnostic as well as prognostic information, as compared to the results from only a few of the other biomarkers. The panel of biomarkers may be on a solid support or in a gel.

In another aspect, the present invention provides a diagnostic kit for diagnosing a dry mucosa condition comprising at least one chemical capable of reacting to at least one biomarker selected from the group consisting of α-enolase, α-1-acid-glycoprotein and prolactin-inducible protein, S100 A8, S100 A9, S100 A4, S100 A11, von Ebner's gland protein, lactoferrin, lysozyme, proline-rich 4 protein and a derivative or fragment thereof. The at least one chemical may be at least one antibody specific for any one of the biomarkers. The at least one chemical may be on a solid support or in a gel. The at least one biomarker may be α-enolase and the at least one chemical is 2-phosphoglycerate. The diagnostic kit may further comprise information pertaining to the use of the kit.

BRIEF DESCRIPTION OF THE FIGURES

FIG. 2A-2J. Comparison of dry eye group (ratio, DE:C, 116:114 and 117:114) and control group (ratio, C2:C1, 115:114) for 10 potential dry eye biomarkers. Student t-tests were performed and p-values are indicated on each graph.

FIG. 3. Protein identification and relative quantification using iTRAQ. (A) MS/MS spectrum of a triply charged peptide ion, TYLISSIPLQGAFNYJ (SEQ ID NO:1) at m/z=701.10 (J represents the iTRAQ-modified lysine residue) which is originated from prolactin-inducible protein. (B) Magnified MS/MS spectrum of 111.0 to 120.0 Da gives signal intensity of four iTRAQ reporter ions at m/z=114.1, 115.1, 116.1 and 117.1 Da. iTRAQ 114 and 115 were used to label 2 control samples and iTRAQ 116 and 117 were used to label 2 dry eye samples. Relative quantitation is based on the ratios of peak areas of reporter ions.

Figure 7A:
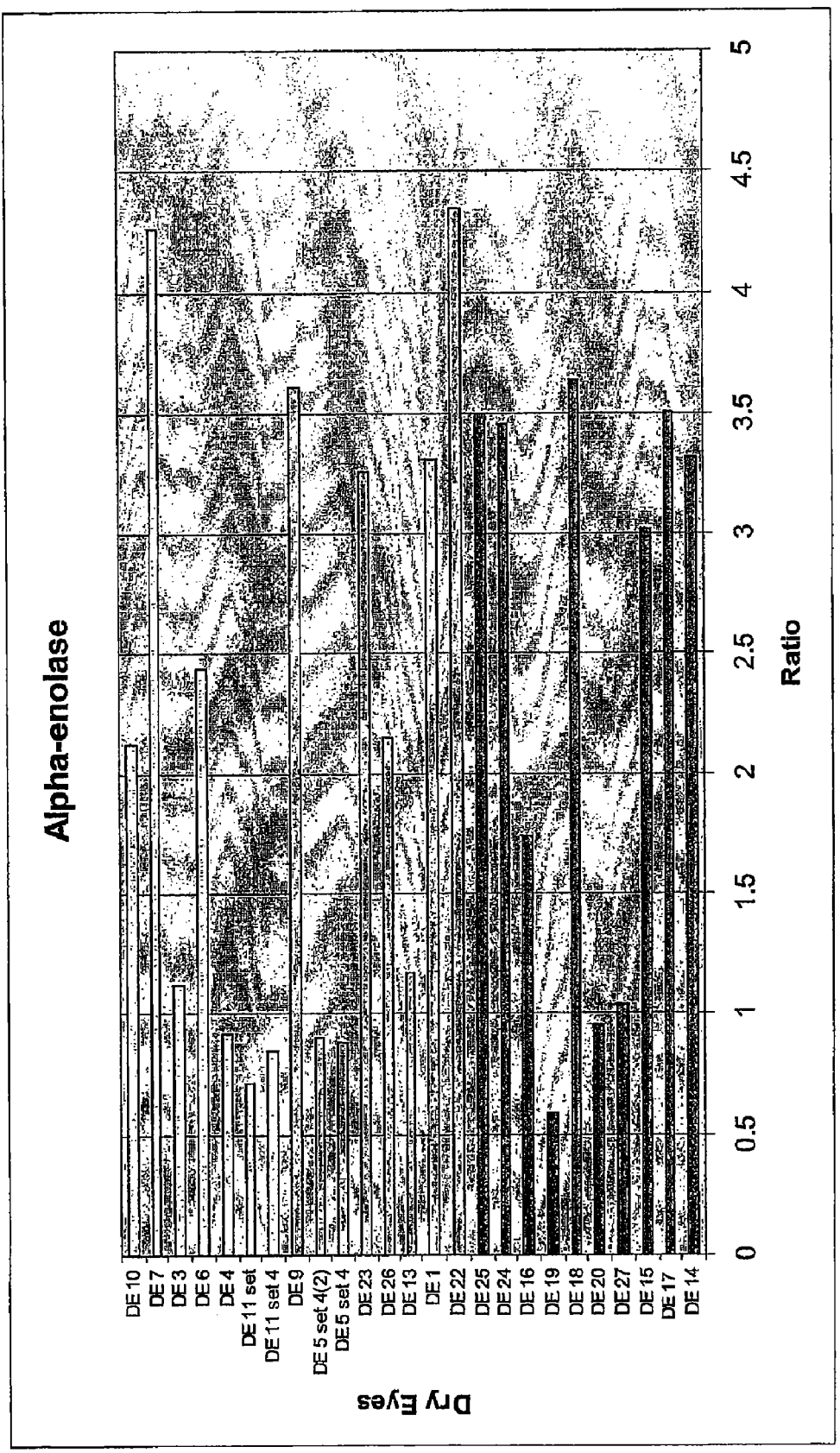
FIG. 7. Ratios (DE:C) were re-organized according to tear break-up time (TBUT) of each patient for (A) α-enolase, (B) α-1-acid glycoprotein 1, (C) S100 A9 and (D) S100 A8. Different color codes were used to distinguish three subgroups.

For FIG. 7A α-enolase
(1) top set of 7 bars in yellow: mild (TBUT=5~10 sec.);
(2) middle set of 8 bars in orange: moderate (TBUT=2~5 sec.);
(3) bottom set of 10 bars in red: severe (TBUT<2 sec.).

Figure 7B:
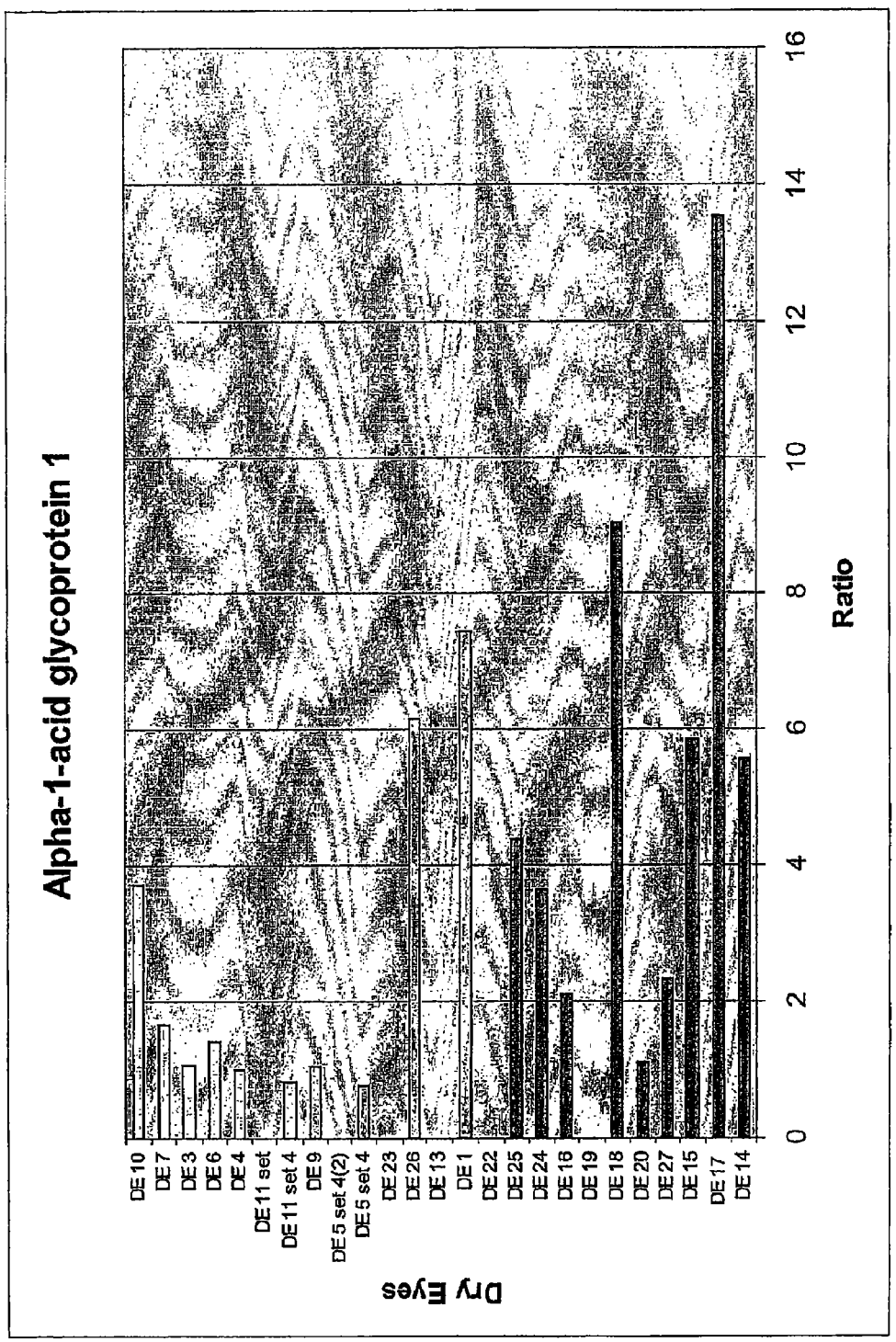

For FIG. 7B α-1-acid glycoprotein 1
(1) top set of 6 bars in yellow: mild (TBUT=5~10 sec.);
(2) middle set of 4 bars in orange: moderate (TBUT=2~5 sec.);
(3) bottom set of 9 bars in red: severe (TBUT<2 sec.).

Figure 7C:
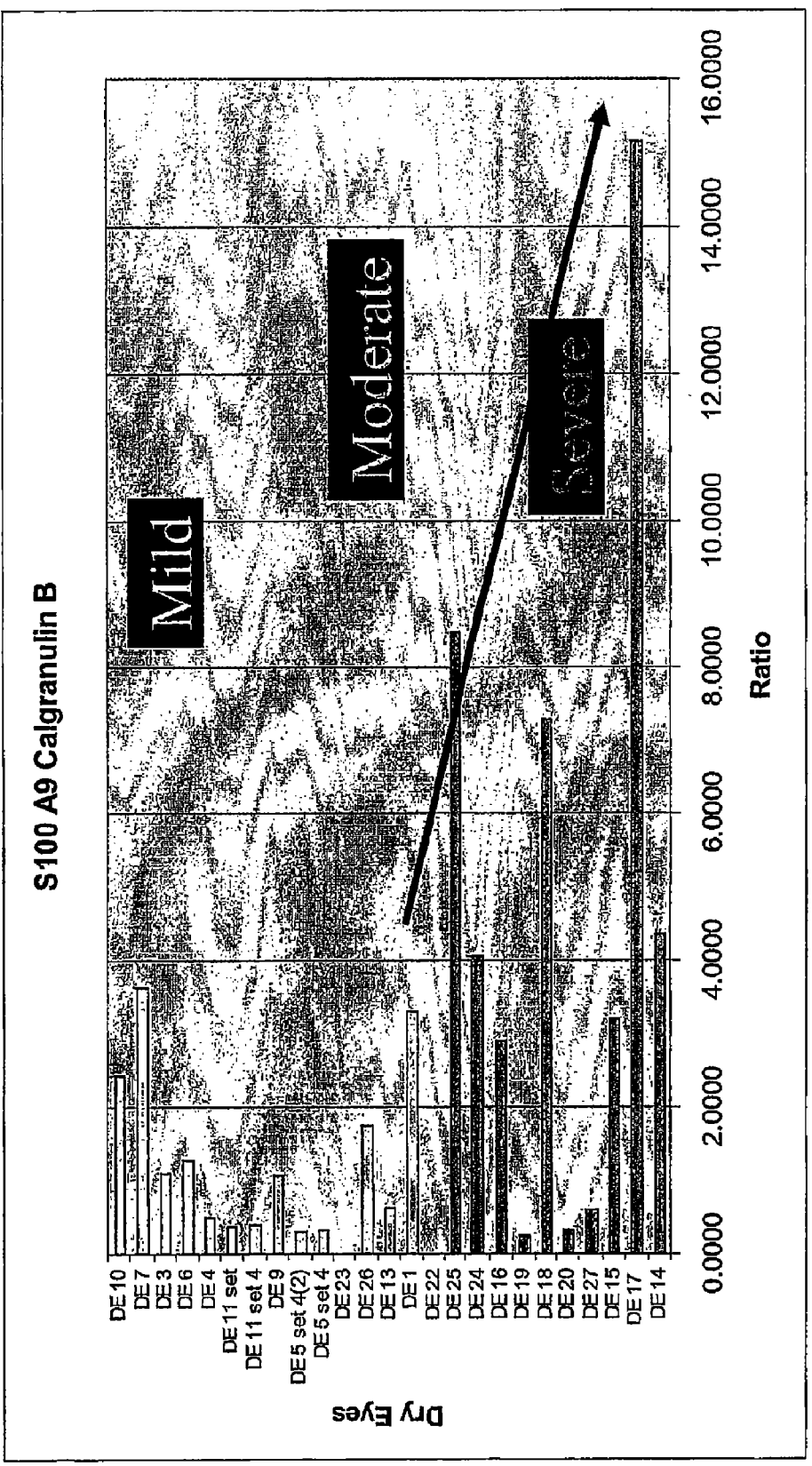

For FIG. 7C S100 A9
(1) top set of 7 bars in yellow: mild (TBUT=5~10 sec.);
(2) middle set of 6 bars in orange: moderate (TBUT=2~5 sec.);
(3) bottom set of 10 bars in red: severe (TBUT<2 sec.).

Figure 7D:
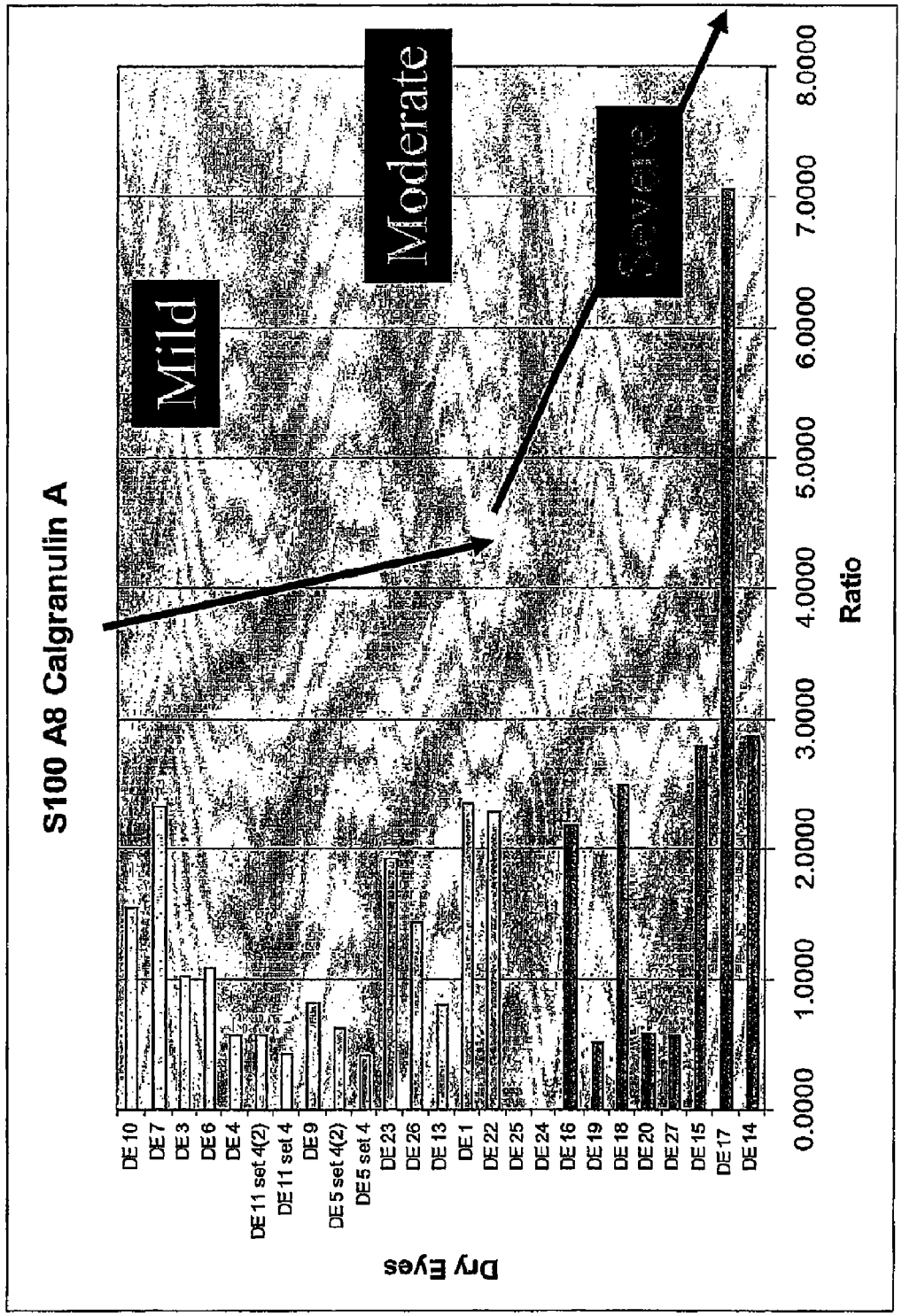

For FIG. 7D S100 A8
(1) top set of 7 bars in yellow: mild (TBUT=5~10 sec.);
(2) middle set of 8 bars in orange: moderate (TBUT=2~5 sec.);
(3) bottom set of 8 bars in red: severe (TBUT<2 sec.).

Figure 8:
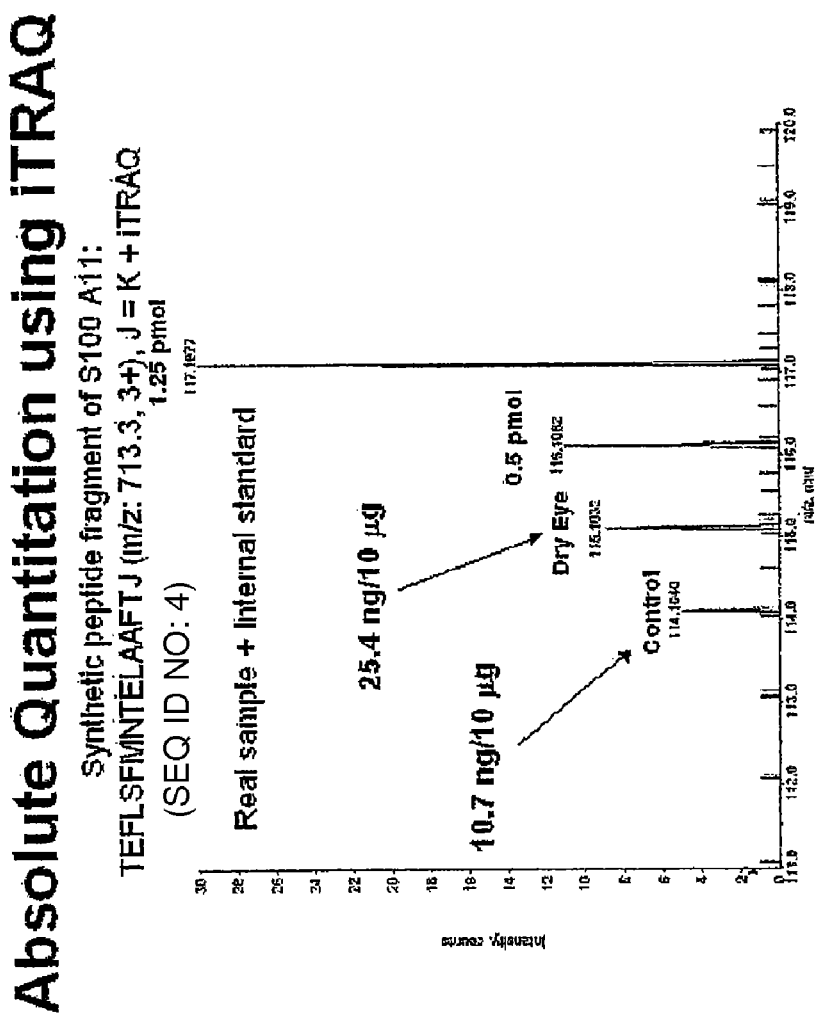

FIG. 8. MS/MS spectrum of reption region (114, 115, 116 and 117) of an iTRAQ experiment for absolute quantitation of one dry eye protein biomarker (S100 A11) in tears.

DETAILED DESCRIPTION

Bibliographic references mentioned in the present specification are for convenience listed in the form of a list of references and added at the end of the examples. The whole content of such bibliographic references is herein incorporated by reference.

DEFINITIONS

Biomarker—Biomarkers are anatomic, physiologic, biochemical, or molecular parameters associated with the presence and severity of specific disease states. Biomarkers are detectable and measurable by a variety of methods including physical examination, laboratory assays and medical imaging. Under the present invention, a protein, protein derivative or protein fragment may be used as a biomarker.

Dryness of mucosa, mucosa dryness condition—A decrease in the natural production or persistence of body fluids that hydrate, lubricate or irrigate the mucosa such that discomfort is felt by the subject experiencing it.

Dry eye—a medical condition due to various causes wherein patient experiences discomfort in the eye due to a decrease in tear fluid production, lack of persistence or loss of the tear fluid produced.

Expression of a biomarker—a qualitative or quantitative indication of a biomarker may be determined from the expression of its gene, gene transcript or gene product in affected cells or tissues. The quantitative indication of a biomarker is reflected in the abundance of its gene, gene transcript or gene product measured. The difference in expression or abundance may be determined between different biomarkers or between the same biomarkers in different subjects. The relative expression or abundance of biomarkers may also be determined between biomarkers or between the same biomarkers in different subjects.

Mucosa/mucous membrane—A membrane lining all body passages, such as the as the underside of the eyelids, the eyeballs, and the respiratory, alimentary and urinary tracts, as well as tissue having cells and associated glands that secrete mucus.

Protein—A biological molecule composed of one or more chains of amino acids in a specific order. Proteins may have derivatives such as isoforms. A protein isoform is a version of a protein with some small differences, usually a splice variant or the product of some post-translational modification. Under the present invention, a protein also encompasses derivatives and fragments that are sufficiently large enough for the protein to be detected, identified and/or quantified by the method(s) used.

Normal range—The normal range of a biomarker is the range of expression or expression of the biomarker in subjects not experiencing or diagnosed with a particular medical condition. Thus, any variation (increase or decrease) of a biomarker from this normal range indicates the medical condition. Under the present condition, statistically significant variation from the normal range of the expression or expression of a biomarker indicates a condition of dry mucosa, such as the condition of dry eye. Under the present invention, variation from the normal range may be determined by running control samples in parallel with test samples. Alternatively, the normal reference range may be pre-determined from a statistically significant number of control samples and values obtained may be compared against this normal reference range.

In one aspect, the present invention relates to a method of diagnosing a dry mucosa condition in a subject, the method comprising: providing a sample from the subject; and comparing expression of at least one biomarker in the sample, the at least one biomarker selected from the group consisting of α-enolase, α-1-acid-glycoprotein, prolactin-inducible protein, S100 A8, S100 A9, S100 A4, S100 A11, von Ebner's gland protein, lactoferrin, lysozyme, proline-rich 4 protein and any of their derivative or fragment thereof with at least one reference value. In another aspect, the present invention provides a method of determining the severity of the condition of dry mucosa in a subject, the method comprising: providing a sample from the subject; and comparing the relative expression of α-1-acid-glycoprotein, S100 A8, S100 A9, S100 A4, S100 A11, lactoferrin, lysozyme, and/or any of their derivative or fragment thereof in the sample and any of their derivative or fragment thereof in the sample with at least one reference value.

In another aspect, the present invention provides a method of monitoring efficacy of a treatment for a dry mucosa condition in a subject, the method comprising: providing a sample from the subject; and comparing expression of at least one biomarker in the sample, the at least one biomarker selected from the group consisting of α-enolase, α-1-acid-glycoprotein and prolactin-inducible protein, S100 A8, S100 A9, S100 A4, S100 A11, von Ebner's gland protein, lactoferrin, lysozyme, proline-rich 4 protein and any of their derivative or fragment thereof.

In another aspect, the present invention provides a method of treating a dry mucosa condition in a subject, the method comprising: providing a sample from the subject; comparing expression of at least one biomarker in the sample, the at least one biomarker selected from the group consisting of α-enolase, α-1-acid-glycoprotein and prolactin-inducible protein, S100 A8, S100 A9, S100 A4, S100 A11, von Ebner's gland protein, lactoferrin, lysozyme, proline-rich 4 protein and any of their derivative or fragment thereof; and reducing the difference in expression of at least one biomarker in the group of biomarkers.

In the above aspects, the dry mucosa condition may be dry eye. The comparing may be with at least one reference value determined from at least one subject not exhibiting signs of, or experiencing symptoms of the dry mucosa condition, and/ or the comparing may be with at least one reference value determined from a statistically significant number of subjects not exhibiting signs of, or experiencing symptoms of the dry mucosa condition. The sample may be a fluid. The expression of the biomarker may be reflected in, or measured by the abundance of the at least one biomarker. The comparing may be by mass spectrometry. The subject may be a human being or a mammal.

Under the method for treating a dry mucosa condition, the at least one biomarker may be α-1-acid-glycoprotein 1 and the reducing of the difference in expression comprises reducing inflammation in the subject. The at least one biomarker may be prolactin-inducible protein and the reducing of the difference in expression comprises increasing the expression of prolactin-inducible protein in the subject by the administration of prolactin and/or androgen. The at least one biomarker may be S100 A8 and S100 A9 and the reducing of the difference in expression comprises reducing the upregulation and/or complex formation, of S100 A8 and S100 A9 in the subject.

In another aspect, the present invention provides a panel of biomarkers for diagnosing the condition of dry eye, the panel comprising α-enolase, prolactin-inducible protein, von Ebner's gland protein, proline-rich 4 protein, and a derivative or fragment thereof. The panel may provide a more detailed profile of the condition, yielding both diagnostic as well as prognostic information, as compared to the results from only a few of the other biomarkers. The panel of biomarkers may be on a solid support or in a gel.

In another aspect, the present invention provides a diagnostic kit for diagnosing a dry mucosa condition comprising at least one chemical capable of reacting to at least one biomarker selected from the group consisting of α-enolase, α-1-acid-glycoprotein and prolactin-inducible protein, S100 A8, S100 A9, S100 A4, S100 A11, von Ebner's gland protein, lactoferrin, lysozyme, proline-rich 4 protein and a derivative or fragment thereof. The at least one chemical may be at least one antibody specific for any one of the biomarkers. The at least one chemical may be on a solid support or in a gel. The at least one biomarker may be α-enolase and the at least one chemical is 2-phosphoglycerate. The diagnostic kit may further comprise information pertaining to the use of the kit.

Under the present invention, the detection, identification, and/or quantification at least one biomarker of a group of biomarkers associated with dry mucosa provides a basis for the diagnosis of a dry mucosa condition. Specifically, the detection, identification, and/or quantification at least one biomarker of a group of biomarkers in tear fluid of a subject provides the basis for diagnosing the condition of dry eyes due to any cause.

Any one or more biomarker of this group of biomarkers may be detected, identified, and/or quantified by one or more suitable methods. Any variation from a normal range of expression of these biomarkers indicates the condition of dry eye, whether or not the subject complains of the condition.

To measure the expression of one or more of these biomarkers, tear fluid is obtained from the subject and biomarkers are detected, identified, and/or quantified. Many methods are available in the art under the present invention such as immunological reactions (eg Enzyme-Linked Immunosorbent Assay) and other biochemical reactions such as enzymatic reactions. Such reactions may comprise detecting the biomarker by photometric means such as a colour change or a difference in absorbance or transmission of light at certain wavelengths.

Another suitable method for use is mass spectroscopy (MS), well known to a person skilled in the art. A modern MS system comprises ionization, detection and analysis means. For analysis of the sample, the system may compare the data obtained from the detection means with known standards to identify the components in the sample, or the system may compare different components within the same sample to derive the results.

Under the present invention, the quantitative proteomics method, iTRAQ technology [6] with 2 dimensional liquid chromatography and tandem mass spectroscopy in the nanoscale (nanoLC-nano-ESI-MS/MS), was combined with statistical analysis and used to detect, identify and quantify biomarkers in the tear fluid of patients diagnosed with dry eye syndrome with a loss of tear secretion. NanoLC-nano-ESI-MS/MS is well known in the art and was developed to separate complex protein mixtures which were previous inadequately performed using one- or two-dimensional polyacrylamide gel electrophoresis (1D or 2D PAGE) [20].

In order attain sufficient confidence in the use of detected biomarkers for the diagnosis of dry eye, stringent criteria are set for the analysis of the MS data followed by statistical analysis to provide indication of the severity of the condition.

Biological functions of the biomarkers under the present invention for the diagnosis of dry mucosa condition are as follows.

α-enolase: α-enolase (ae) is one of the key glycolytic enzymes that is expressed abundantly in many cells. However, more recently it was also found on the cell surface as a surface protein [7] in such cells as hematopoietic cells (neutrophils, B cells, T Cells, monocytes), epithelial cells, neuronal cells, etc. In addition to its innate glycolytic function, α-enolase has been recognized as a multifunctional protein. Very recent studies indicate that it may play an important role in several disease processes, for example, many autoimmune disorders, cancer, systemic fungal disease and dental diseases. However, this is the first report of the presence of α-enolase in tear fluid.

α-1-acid glycoprotein 1: α1-acid glycoprotein 1 (AGP) is a heavily glycosylated protein (45%) with a molecular weight of 41-43 kDa [8]. It also belongs to the lipocalin family. It is associated with inflammatory responses. The synthesis is controlled by glucocorticoids, interleukin-1 and interleukin-6. Its anti-inflammatory effects were noted. AGP exhibits both pro- and anti-inflammatory effects. These dual immunomodulatory effects may indicate that AGP plays an important role in the regulation of immune response and inflammation. This is also the first report of detecting α1-acid glycoprotein 1 in tear fluid.

S100 A8 and S100 A9: S100 A8 and A9 belong to S100 calcium-binding protein family. There is growing evidence to show that S100 A8, A9 and A12 form a new group of pro-inflammatory proteins [9]. In inflammatory diseases, the over-expression of both S100 A8 and S100 A9 are typically seen. They are secreted at sites of inflammation. The over-expression of only S100 A8 in dry eye tears has been previously reported [10]. These two proteins can form complexes which induces apoptosis when present in high concentrations.

S100 A4: S100 A4 is a member of S100 calcium binding protein family. The best known role of S100 A4 is its ability to cause cell shape changes. More recently [11], it was shown that S100 A4 is capable of stimulating corneal neovascularization in vivo. S100 A4 also appears to take part in the homeostasis of growth, with apparent involvement in growth factor signal transduction and apoptotic cell death. There is considerable evidence that S100 A4 expression alters the adhesion properties of cells, possibly by remodelling the extra-cellular matrix and promoting a redeployment of adhesion-mediating macromolecules occurring in the extracellular matrix [12].

S100 A11: This is another member in S100 calcium binding protein family. S100 A11 seems to be involved in apoptosis [13].

Lactoferrin and lysozyme: These are well known, abundant human tear proteins. They both have anti-bacterial activity on the ocular surface. In previous studies, the down-regulation of these two tear proteins was observed in patients with dry eye [14, 10].

von Ebner's gland protein: von Ebner's gland protein, also called tear specific prealbumin (TSPA) or tear lipocalin [15], is one of the major tear proteins and acts as the principal lipid binding protein. It is regarded as general protection factor for the epithelial surface.

Prolactin-inducible protein: Prolactin-inducible protein (PIP) is typically expressed in several exocrine tissues, such as the lacrimal, salivary, and sweat glands and may also be associated with breast cancer [16]. A very recent study showed that it is down-regulated in tears of blepharitis patients but this would be the first reported association with dry eye [17].

Proline-rich 4 protein: It is also regarded as one of the abundant tear proteins recently [18, 10]. Proline-rich protein 4 is expressed abundantly in lacrimal gland where it is found in the acinar cells [19]. It may reflect the function of the acinar cells. It has been shown to be down-regulated in dry eye patients [10].

Once diagnosis of a dry mucosa condition such as dry eye is made using the method of the present invention, it will be possible to also use the method to monitor the efficacy of a treatment for the condition. A subject may be prescribed a course of treatment and monitored at intervals by periodic determination of the expression of one or more of the biomarkers of the present invention. The type and duration of treatment of such dry mucosa conditions and the interval and duration of monitoring of the efficacy of treatment will be known to a person skilled in the art such as a physician. The method of present invention may also be used to monitor the efficacy of a new treatment method in drug trials.

The present invention also provides a method to treat a dry mucosa condition by countering the causes of variation of one or more of the biomarkers of the present invention to return the expression of one or more of the biomarkers back to the normal range.

The present invention also provides a panel of biomarkers for the diagnosis and to profile a dry mucosa condition. While the expression of several biomarkers may be changed by the medical condition, the panel of biomarkers provides more specific and precise diagnosis of the condition. When the biomarkers on the panel are measured, the relative expression or abundance of the biomarkers on the panel to each other can indicate the severity of the condition.

The present invention also provides a diagnostic kit for the diagnosis of a dry mucosa condition such as dry eye. The kit comprises at least one chemical capable of reacting with one or more biomarkers such that the reaction may be detected. For example, the chemical may be an antibody that specifically binds to a biomarker. Alternatively, the chemical may be a substrate for the biomarker. These chemicals may be on a support such as a solid support or a gel. The diagnostic kit may give a qualitative and/or quantitative result that allows the medical condition to be diagnosed.

Having now generally described the invention, the same will be more readily understood through reference to the following examples which are provided by way of illustration, and are not intended to be limiting of the present invention.

EXAMPLES

Methods

Example 1

Patients

A total of 28 patients clinically diagnosed with dry eye syndrome and 20 control subjects with no other ocular diseases were recruited. Informed consent was obtained from all participating subjects and the whole procedure was approved by Institutional Review Board committee of Singapore Eye Research Institute (SERI) and also adhered to the tenets of the Declaration of Helsinki. Clinical examinations included subjective symptoms, Schirmer test (without anesthesia), tear break-up time (TBUT) test, and other general ophthalmic examinations such as visual acuity and lid margin and meibomian gland appraisal. Typical affective symptoms for dry eye include burning, itching and stinging, foreign body sensation, sense of dryness, blurring of vision, photophobia, pain and heavy or tired eyes. Patients were classified as having dry eye based on the Schirmer test, TBUT, and subjective symptoms.

Example 2

Collection and Tear Protein Elution

Tear fluids for all patients were collected using the Schirmer strip. For this test, a thin tear strip (of paper) is placed inside the lower eyelid for 5 mins without anesthesia. Tears collected were subsequently eluted off of the strip. The ability to do this was critical as the reduction in tears made it impractical to collect tears using the capillary method. After collection, Schirmer strips were immediately frozen at −80° C. until analysis. The first 10 mm of Schirmer strip was cut into small pieces and soaked in 150 µl of phosphate-buffered saline (PBS) for 3 hours to elute the tear proteins from the Schirmer strip. Total tear protein concentrations were then measured using a Micro BCA Protein Assay Kit (Pierce Biotechnology, Inc.) for each sample.

Example 3

Study Design and iTRAQ (Isobaric Tags for Relative and Absolute Quantification iTRAQ) Sample Preparation Since iTRAQ technology allows labeling 4 samples simultaneously, 2 controls (C) and 2 dry eye samples (DE) were used in each set (a total of 14 sets). In these 14 sets, individual control samples were used in 9 sets and pooled control samples (one pooled from 5 controls and one pooled from 3 controls) were used in another 5 sets of experiments. 30 µg from each sample was used for the iTRAQ experiments. The iTRAQ procedure was followed according to the protocol provided by Applied Biosystems (Foster City, Calif.). Here, 20 µl of Dissolution Buffer (triethylammonium bicarbonate) and 1 µl of Denaturant (2% SDS) from the iTRAQ reagent kit were added to the samples. Then 2 µl of Reducing Reagent (tris-(2-carboxyethyl)phosphine) was then added and the samples incubated at 60° C. for 1.5 h. In the next step 1 µl of Cysteine Blocking Reagent (methyl methanethiosulfonate) was added and incubated at room temperature for 20 min. The samples were then digested at 37° C. overnight with trypsin. iTRAQ reagents 114 and 115 were added to the control samples while iTRAQ reagents 116 and 117 were added to the dry eye samples. The samples were then incubated at room temperature for 3 h. The contents of each iTRAQ reagent labeled sample were combined and dried using a SpeedVac concentrator. For testing, 10 µl of loading buffer (0.1% formic acid, 2% acetonitrile in water) was added to reconstitute the sample before performing the 2D nano-LC-nano-ESI-MS/MS analysis.

Example 4

Two Dimensional Nano-LC-Nano-ESI-MS/MS Analysis

Two dimensional nanoLC (DIONEX, LC Packings, Sunnyvale, Calif.) coupled with nano-ESI-MS/MS (Applied Biosystems, Q-StarXL, MDS Sciex, Concord, Ontario, Canada) was used for the analysis. The two dimensional LC separation of peptides is the most common configuration which consists of a strong cation exchange (SCX) followed by reverse phase (RP) chromatography. SCX column used in the first dimension was from DIONEX, LC Packings (300 µm i.d.×10 cm porosity 10S SCX).

Elution of the peptide mixture was performed using 10 steps of increasing salt concentrations (20 µl injection of 10 mM, 20 mM, 30 mM, 40 mM, 50 mM, 75 mM, 100 mM, 250 mM, 500 mM and 1000 mM ammonium acetate) all at a flow rate of 30 µl/min and using a loading solvent of 0.1% formic acid/ACN (95:5, v:v). RP column used in the second dimension was a 10 cm×75 µm i.d. microcapillary LC column self-packed from a self-pack PicoFrit (360 µm OD, 75 µm ID, 50 cm, New Objectives, Woburn, Mass.). This capillary column was packed with Luna C18, 3 µm, 100 Å from Phenomenex (Torrance, Calif.) using a home-made column packing device. The capillary column had an integrated spray tip (15 µm opening) which can be directly coupled with the nanospray interface (Protana, Odense, Denmark) into ABI's Q-TOF mass spectrometer.

After SCX separation, the sample was loaded onto a trapping cartridge (C18, 0.3×5 mm, from DIONEX, LC Packings) from a Famos autosampler (DIONEX, LC Packings) at 30 µL/min for desalting. After a 5 min wash with acetonitrile/water (2/98, v/v with 0.1% formic acid), the system was switched (Switchos, DIONEX, LC Packings) into line with the RP analytical capillary column. Using an Ultimate solvent delivery system (DIONEX, LC Packings), a linear gradient of acetonitrile (0.1% formic acid) from 20% to 95% over 85 min at flow rate of ~300 mL/min was used to analyze the tryptic digests. Key parameter settings for the nanospray and other instrumentation were as follows: ionspray voltage (IS)=2200 V, curtain gas (CUR)=20, declustering potential (DP)=60 V, focusing potential (FP)=265 V, collision gas setting (CAD)=5 for nitrogen gas, DP2=15.

All data was acquired using information-dependent acquisition (IDA) mode with Analyst QS software (Applied Biosystems). For IDA parameters, 1 sec time of flight (TOF) mass spectrometry (MS) survey scan in the mass range of 300~1200 followed by two product ion scans of 3 sec each in the mass range of 100~1500. The "enhance all" function was used in the IDA experiments. Switching criteria were set to ions greater than a mass-charge ratio (m/z)=350 and smaller than m/z=1200 with charge state of 2 to 4 and an expression threshold of >20 counts/s. Former target ions were excluded for 60s. IDA collision energy (CE) parameters script was used for automatically controlling the CE.

Example 5

Data Analysis

Data analysis for the iTRAQ experiments was performed using ProQUANT 1.0, together with ProGroup View 1.0 (Applied Biosystems) and searched against the IPI (International Protein Index) human database v3.15. The mass tolerance set for peptide identification in ProQUANT searches were 0.15 Da for MS and 0.10 Da for MS/MS, respectively. The cut off for the confidence settings was at 75. Other search parameters include MMTS (methyl methanethiosulfonate) as the cysteine fixed modification, 1 missed trypsin cleavage site, oxidation to methionine in the zone modifications and custom amino acids with iTRAQ modification to lysine and tyrosine.

The results generated by Pro Quant were then analyzed and summarized by Pro Group Viewer 1.0 (Applied Biosystems) to produce a ProGroup Report. The protein identification criteria are as follows: (a) proteins with ProtScore>2 (>99% confidence) were all accepted; (b) proteins with ProtScore=2 (=99% confidence), typically one peptide with confidence of 99%, were accepted with manually verified MS/MS spectra. For differential expression, a bias correction factor was applied for correcting possible pipetting error during the combination of differentially labeled samples.

Relative quantification of proteins using iTRAQ technology is based on the ratio of peak areas of m/z 114, 115, 116 and 117 Da from MS/MS spectra. Since 2 controls (C1 and C2) were tagged with 114 and 115 and 2 dry eye samples (DE1 and DE2) were tagged with 116 and 117, the relative quantitative result can be expressed as DE1:C1, DE2:C1, DE1:C2, DE2:C2, C1:C2 and C2:C1 using ratio. For the quantitative results, besides reporting ratios, Pro Group also gives p-value and Error Factor (EF). Smaller p-value (on a scale of 0 to 1) often means more confidence about the altered expression (non-unity ratios, for example, diseased sample vs normal sample) resulting from a real biological difference. The EF expresses the 95% uncertainty range for any reported ratio.

Example 6

Statistical Analysis (a) Calculation of Average of Ratios:

To obtain an average of ratios for a particular protein from 14 sets of iTRAQ data, we used weighted average calculation by involving EF. Firstly we converted the ratios to log space [log(ratio)]. Then the log of the EF and we used the inverse of the EF as the weight. The weighted average in log space was calculated using the following formula:

Weight average (log space)=Sum [log(ratio)×weight]/ Sum (weight), where, weight=1/log EF.

Finally we convert it back out of log space to find the "weight average of the ratios".

(b) Finding Significant Changes by T-Test:

The ratios were divided into two groups, i.e. dry eye group (DE1:C1, DE2:C1, DE1:C2, DE2:C2) and control group (C1: C2 and C2:C1). Data from 14 sets of iTRAQ experiments were combined and student t-tests were performed to calculate the p-values to evaluate whether the changes between dry eye group and control group are significant ($p<0.05$ was considered as significant change).

Figure 1:
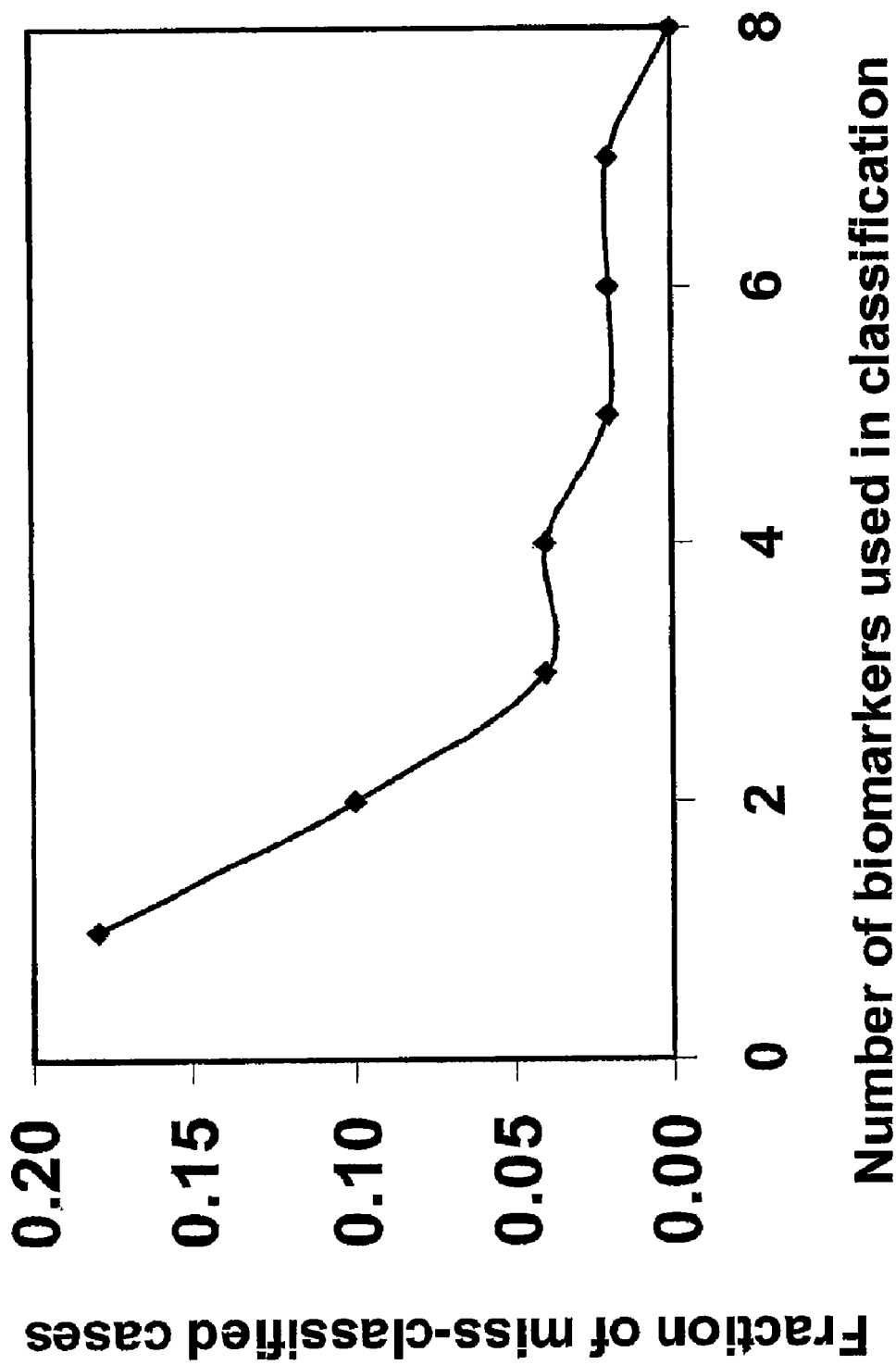
FIG. 1. Relation between fraction of misclassified cases and number of biomarkers used.
Figure 2A:
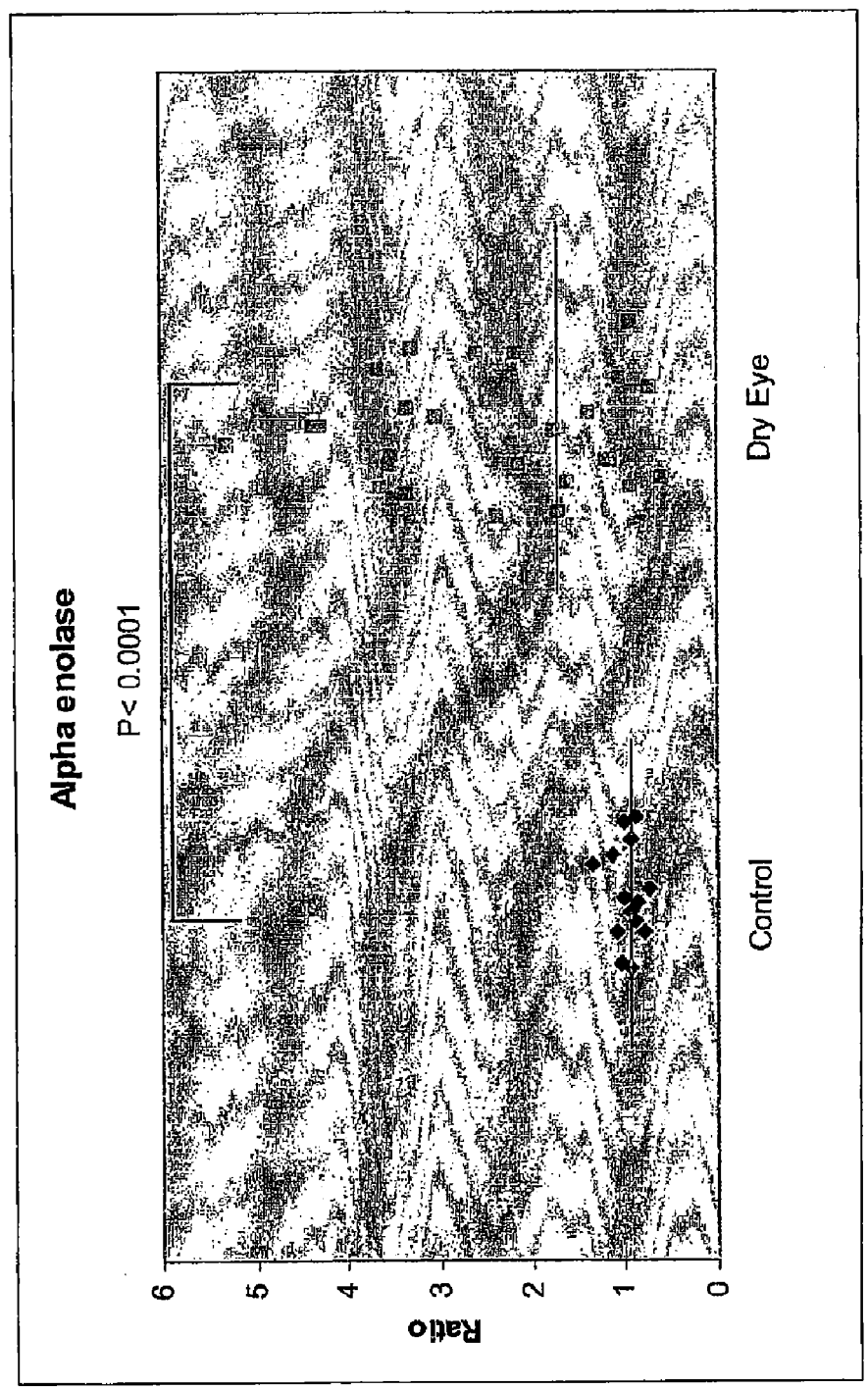
Figure 2B:
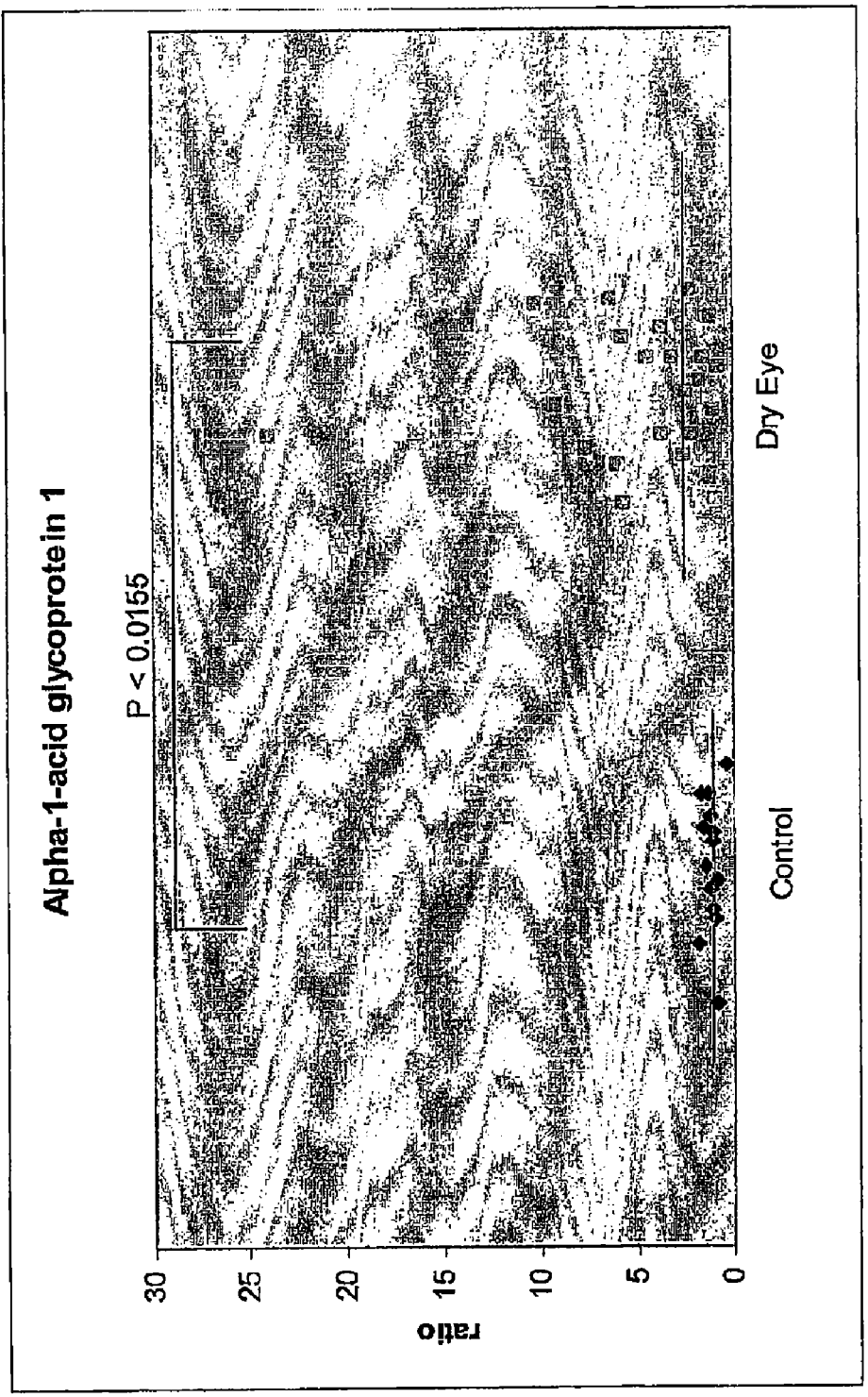
Figure 2D:
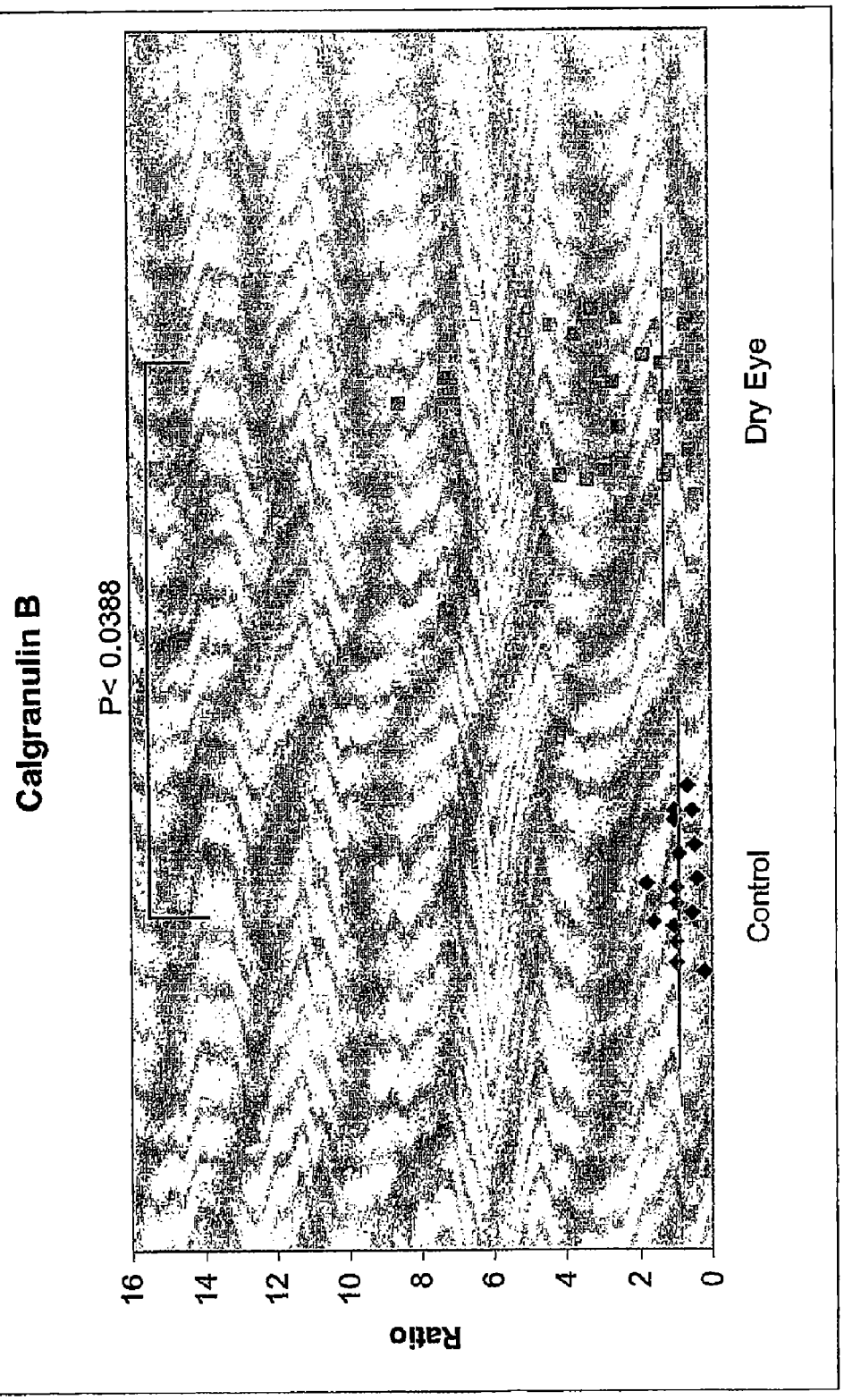
Figure 2E:
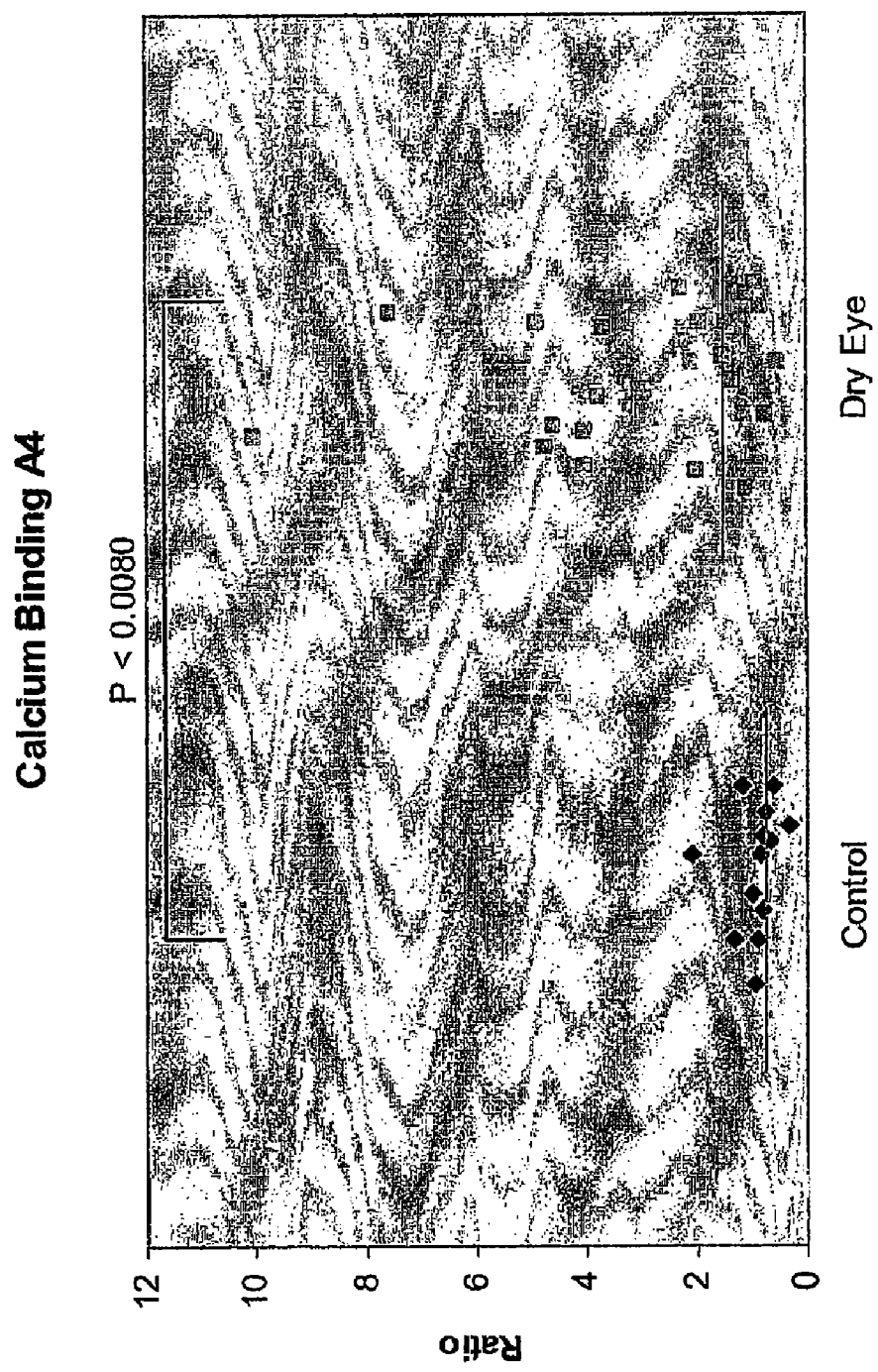
Figure 2G:
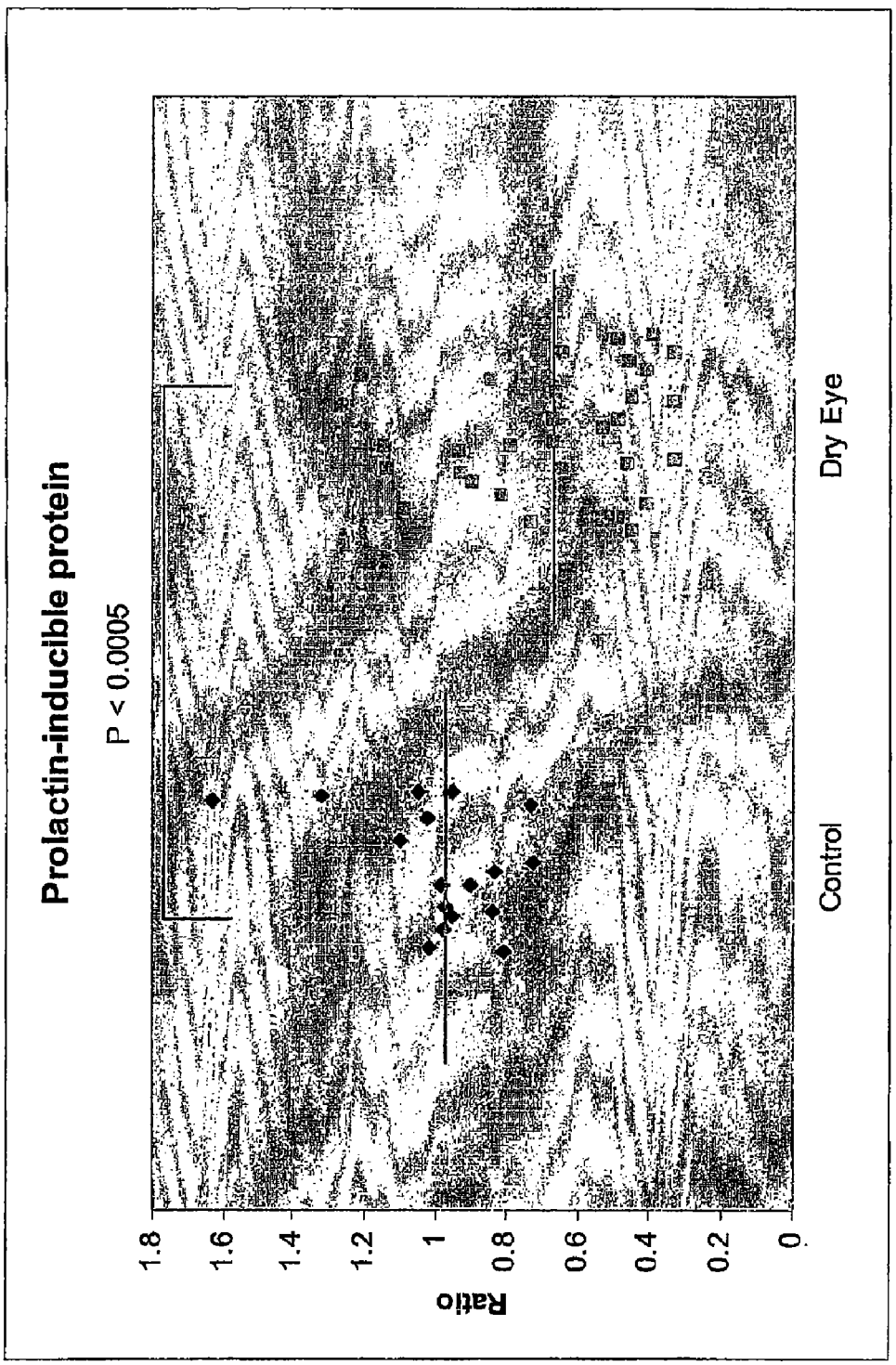
Figure 2H:
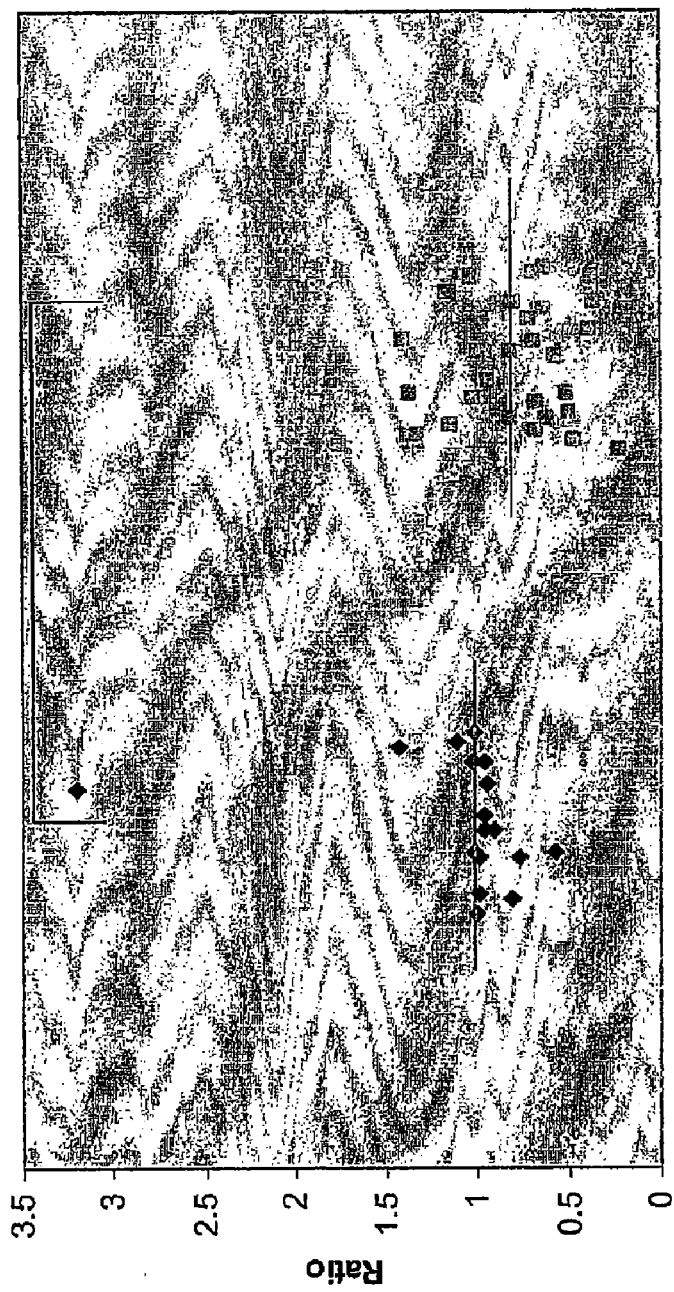
Figure 2I:
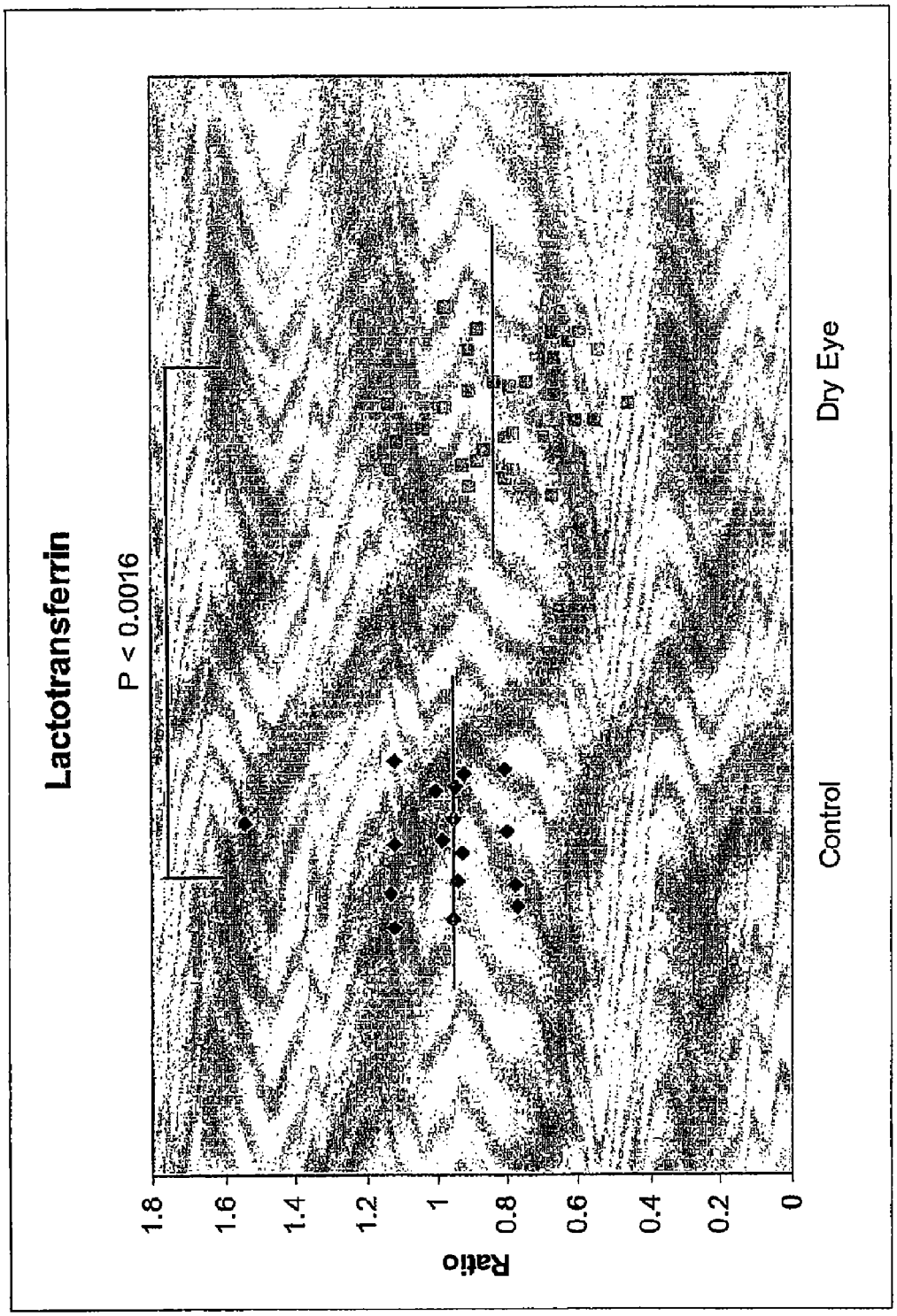
Figure 2J:
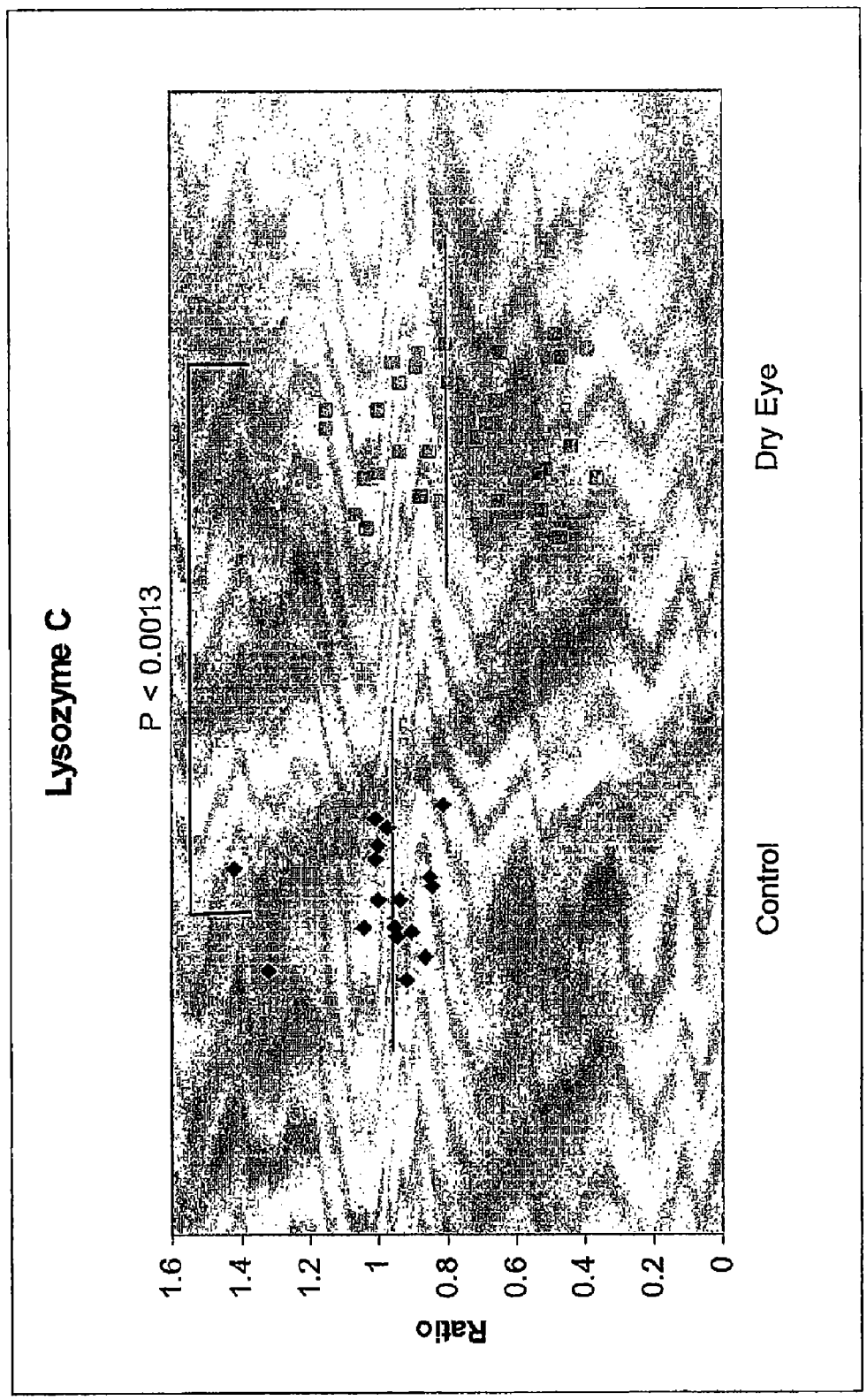

(c) Selection of a Biomarker Panel:

Posterior to t-test, 10 biomarker candidates were selected based on their p-values<0.05. Proline-rich protein 4 was also taken as a biomarker since it was reported in literature [10]. Linear classifiers were used to determine the best combination of those biomarker candidates to form a biomarker panel. First, the receive operation characteristic (ROC) curves were obtained for individual biomarker candidates. The first ranked biomarker candidate (α-enolase) was taken and used for identification of dry eye cases. For those samples which were classified as negatives by α-enolase, linear classifiers using a combination of up to any eight of the remaining 10 biomarker candidates were constructed. The selection of the optimal panel of biomarkers was determined by the performance curve of different numbers of biomarker candidates (FIG. 1). As a result, a linear combination of three proteins (p0, p1 and p2)

$$y=\log 2 \text{ ratio}\_p0 + a1 \log 2 \text{ ratio}\_p1 + a2 \log 2 \text{ ratio}\_p2$$

was used for further distinguishing dye eye cases from normal cases. The parameters a1 and a2 were determined based on optimization of the ROC accuracy (area under ROC curve).

Results

Example 7

Tear Protein Identification

A total of 64 tear proteins were identified from 14 sets of iTRAQ experiments using highly stringent criteria for protein identification (ProtScore>2, >99% confidence). With this threshold, typically no less than two peptides with high confidence were used for protein identification. In ProGroup View, each peptide can contribute no more than 2.0 to the ProtScore (equivalent to no higher confidence than 99.0%). Table 1 gives the protein identification list with total ProtScore and number of peptides identified for each protein.

TABLE 1

Summary of identified tear proteins. (ProtScore >2, >99% confidence)0

| No. | Accession No. | Protein Name | No. of Peptides Identified |
|---|---|---|---|
| 1 | IPI00000816 | 14-3-3 protein epsilon | 2 |
| 2 | IPI00007427 | AGR2 (Anterior gradient protein 2 homolog) | 2 |
| 3 | IPI00022434 | ALB protein (Serum albumin) | 47 |
| 4 | IPI00022429 | Alpha-1-acid glycoprotein 1 precursor | 2 |
| 5 | IPI00020091 | Alpha-1-acid glycoprotein 2 precursor | 2 |
| 6 | IPI00550991 | Alpha-1-antichymotrypsin precursor | 1* |
| 7 | IPI00553177 | Alpha-1-antitrypsin precursor | 9 |
| 8 | IPI00465248 | Alpha-enolase | 9 |
| 9 | IPI00218918 | Annexin A1 | 2 |
| 10 | IPI00455315 | Annexin A2 | 2 |
| 11 | IPI00008580 | Antileukoproteinase 1 precursor | 2 |
| 12 | IPI00024284 | Basement membrane-specific heparan sulfate proteoglycan core protein precursor | 4 |
| 13 | IPI00004656 | Beta-2-microglobulin precursor | 2 |
| 14 | IPI00027463 | Calcyclin (S100 calcium-binding protein A6) | 3 |
| 15 | IPI00013895 | Calgizzarin (S100 calcium-binding protein A11) | 2 |
| 16 | IPI00007047 | Calgranulin A (S100 calcium-binding protein A8) | 9 |
| 17 | IPI00027462 | Calgranulin B (S100 calcium-binding protein A9) | 11 |
| 18 | IPI00021828 | Cystatin B | 2 |
| 19 | IPI00032294 | Cystatin S precursor | 7 |
| 20 | IPI00553058 | Deleted in malignant brain tumors 1 | 3 |
| 21 | IPI00020487 | Extracellular glycoprotein lacritin precursor | 7 |
| 22 | IPI00479359 | Ezrin | 2 |
| 23 | IPI00247167 | F-box associated region domain containing protein | 2 |
| 24 | IPI00027497 | Glucose-6-phosphate isomerase | 2 |
| 25 | IPI00219757 | Glutathione S-transferase P | 3 |
| 26 | IPI00641737 | Haptoglobin | 7 |
| 27 | IPI00025512 | Heat-shock protein beta-1 | 2 |
| 28 | IPI00022488 | Hemopexin precursor (Beta-1B-glycoprotein) | 5 |
| 29 | IPI00644694 | Ig alpha-1 chain C region | 13 |
| 30 | IPI00642363 | Ig alpha-2 chain C region | 10 |
| 31 | IPI00550702 | Ig gamma-1 chain C region | 9 |
| 32 | IPI00647471 | Ig gamma-2 chain C region | 4 |
| 33 | IPI00642193 | Ig gamma-4 chain C region | 2 |
| 34 | IPI00641082 | Ig kappa chain C region | 6 |
| 35 | IPI00552445 | Ig lambda chain C regions | 8 |
| 36 | IPI00549291 | IGHM protein | 3 |
| 37 | IPI00178926 | Immunoglobulin J chain | 6 |
| 38 | IPI00382577 | Kappa 1 light chain variable region | 2 |
| 39 | IPI00025023 | Lactoperoxidase precursor | 5 |
| 40 | IPI00298860 | Lactotransferrin precursor | 57 |
| 41 | IPI00027444 | Leukocyte elastase inhibitor | 2 |
| 42 | IPI00465431 | LGALS3 protein (Galectin-3) | 2 |
| 43 | IPI00009650 | Lipocalin-1 precursor | 14 |
| 44 | IPI00001468 | Lipophilin-A precursor | 3 |
| 45 | IPI00019038 | Lysozyme C precursor | 15 |
| 46 | IPI00026126 | Mammaglobin-B precursor | 8 |
| 47 | IPI00299547 | Neutrophil gelatinase-associated lipocalin precursor (Lipocalin-2) | 2 |
| 48 | IPI00419585 | Peptidyl-prolyl cis-trans isomerase A | 2 |
| 49 | IPI00000874 | Peroxiredoxin-1 | 3 |
| 50 | IPI00004573 | Polymeric-immunoglobulin receptor precursor | 16 |
| 51 | IPI00022974 | Prolactin-inducible protein precursor | 11 |
| 52 | IPI00009682 | Proline-rich protein 1 precursor | 5 |
| 53 | IPI00027019 | Proline-rich protein 4 precursor | 7 |
| 54 | IPI00032313 | S100 calcium-binding protein A4 | 3 |
| 55 | IPI00022463 | Serotransferrin precursor | 17 |
| 56 | IPI00164623 | Similar to Complement C3 precursor | 4 |
| 57 | IPI00294578 | Splice Isoform 1 of Protein-glutamine gamma-glutamyltransferase 2 | 1* |
| 58 | IPI00018230 | Submaxillary gland androgen-regulated protein 3 homolog A precursor (Proline-rich protein 5) | 2 |
| 59 | IPI00023011 | Submaxillary gland androgen-regulated protein 3 homolog B precursor (Proline-rich protein 3) | 2 |
| 60 | IPI00216298 | Thioredoxin | 2 |
| 61 | IPI00299729 | Transcobalamin I precursor | 2 |
| 62 | IPI00719422 | Triosephosphate isomerase | 2 |
| 63 | IPI00011694 | Trypsin-1 precursor | 2 |
| 64 | IPI00166729 | Zinc-alpha-2-glycoprotein precursor | 19 |

*Only one of 2 peptides were found to have a good MS/MS match when the spectra were searched using Mascot.

Example 8

Relative quantitation of tear proteins comparing dry eye patients with normal controls by iTRAQ technology and discovery of potential biomarkers Overall, statistical analysis showed that in total, 10 proteins were differentially expressed between the dry eye group and the normal control group with 6 proteins up-regulated and 4 proteins down-regulated in dry eye patients. The ratios, p-values and EF for the 10 dry eye biomarkers from these 14 sets are given below.

Six up-regulated proteins were found: α-enolase, α-1-acid glycoprotein 1, S100 A8 (calgranulin A), S100 A9 (calgranulin B), S100 A4 and S100 A11 (calgizzarin) and 4 down-regulated proteins: prolactin-inducible protein (PIP), von Ebner's gland protein (tear specific prealbumin, lipocalin), lactoferrin and lysozyme (see FIG. 2). Table 2 summarizes the weighted average ratios and p-value of the above 10 proteins for the control group and dry eye group. Among these 10 biomarkers, α-enolase, α-1-acid glycoprotein 1, S100 A9, S100 A4, S100 A11 and prolactin-inducible protein have never been reported previously. FIGS. 3-5 show three representative MS/MS spectra for prolactin-inducible protein, α-enolase and α-1-acid glycoprotein 1, which give both identification and quantitative information.

TABLE 2

Summary of weighted average ratios (DE:C and C2:C1) and p-values of potential biomarkers for control group and dry eye group.

| Protein Name | Control (C2:C1) (Weighted average ratio) | Dry Eye (DE:C) (Weighted average ratio) | P-Value |
| --- | --- | --- | --- |
| Alpha-enolase | 0.933 | 1.698 | 0.0001 |
| S100A8 Calgranulin A | 0.933 | 1.259 | 0.0337 |
| S100A9 Calgranulin B | 0.891 | 1.202 | 0.0388 |
| Alpha-1-acid glycoprotein | 1.230 | 2.512 | 0.0155 |
| S100A11 Calgizzarin | 0.977 | 1.660 | 0.0550 |
| S100 A4 Calcium-Binding protein | 0.759 | 1.479 | 0.0080 |
| Lactotransferrin | 0.955 | 0.832 | 0.0016 |
| Von Ebner's gland protein | 1.000 | 0.813 | 0.0172 |
| Prolactin-inducible protein | 0.955 | 0.661 | 0.0005 |
| Lysozyme C | 0.955 | 0.794 | 0.0013 |
| Proline-rich 4 protein | 1.023 | 0.912 | 0.4336 |

Figure 4A:
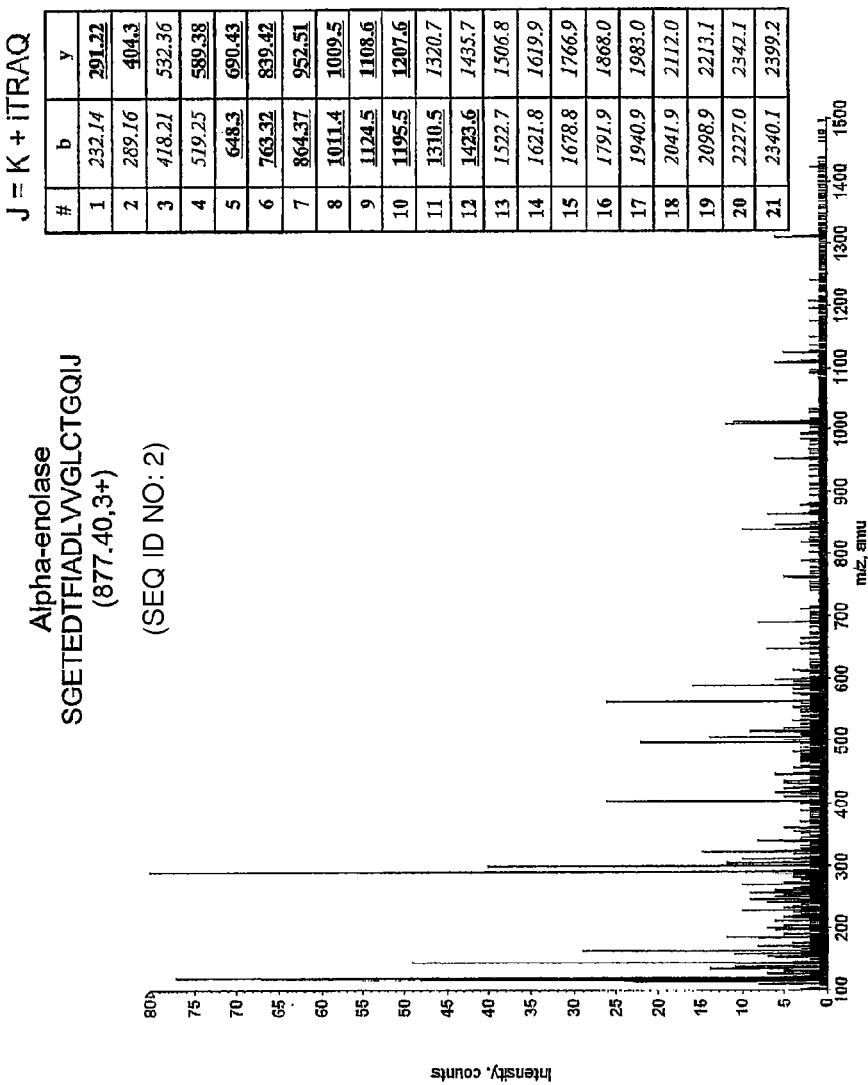
FIG. 4. (A) MS/MS spectrum of one triply charged peptide ion (SGETEDFIADLWGLCTGQIJ (SEQ ID NO:2) at m/z=877.40 Da) originated from α-enolase and (B) relative quantification for α-enolase between dry eye samples and control samples.
Figure 4B:
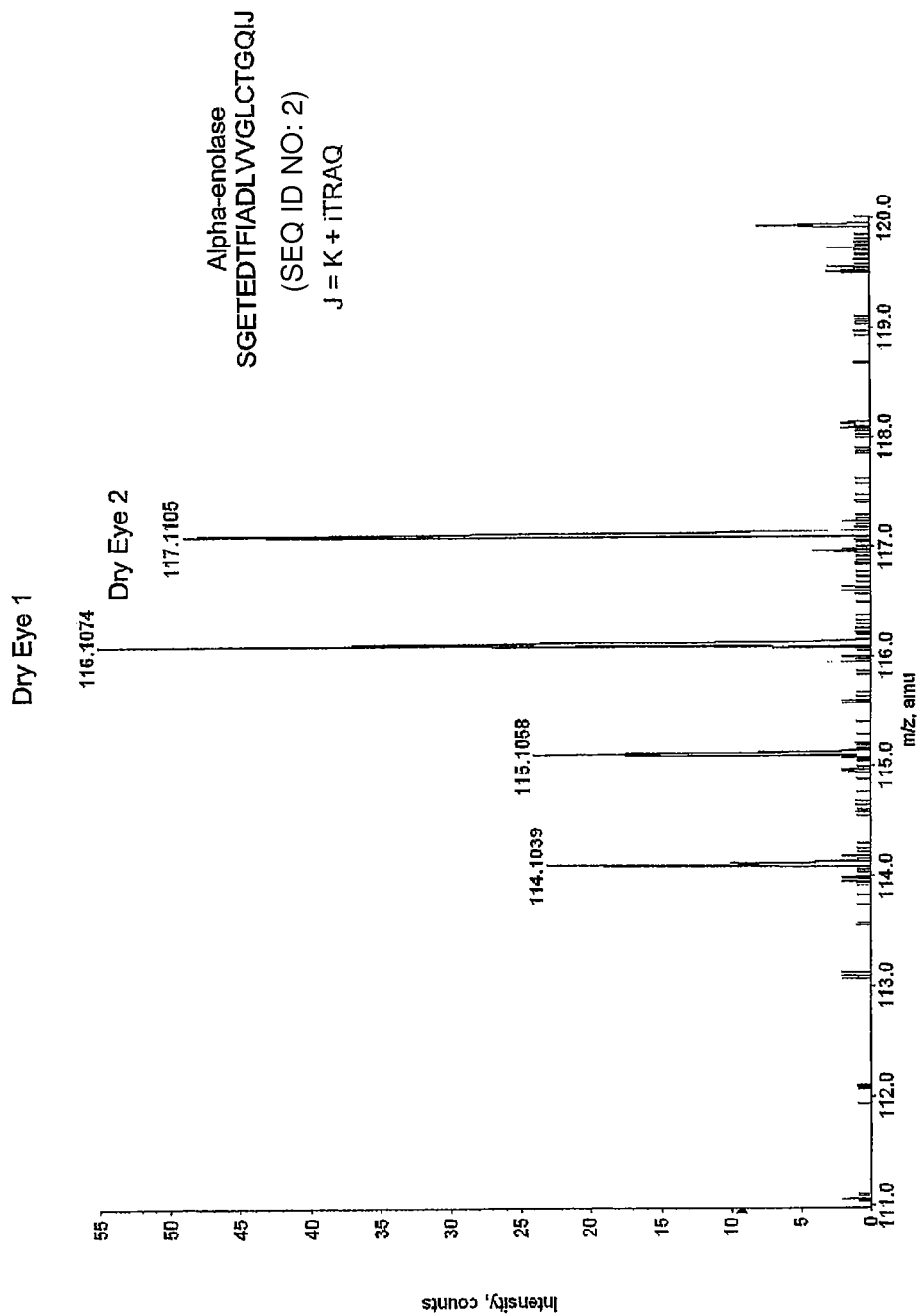
Figure 5A:
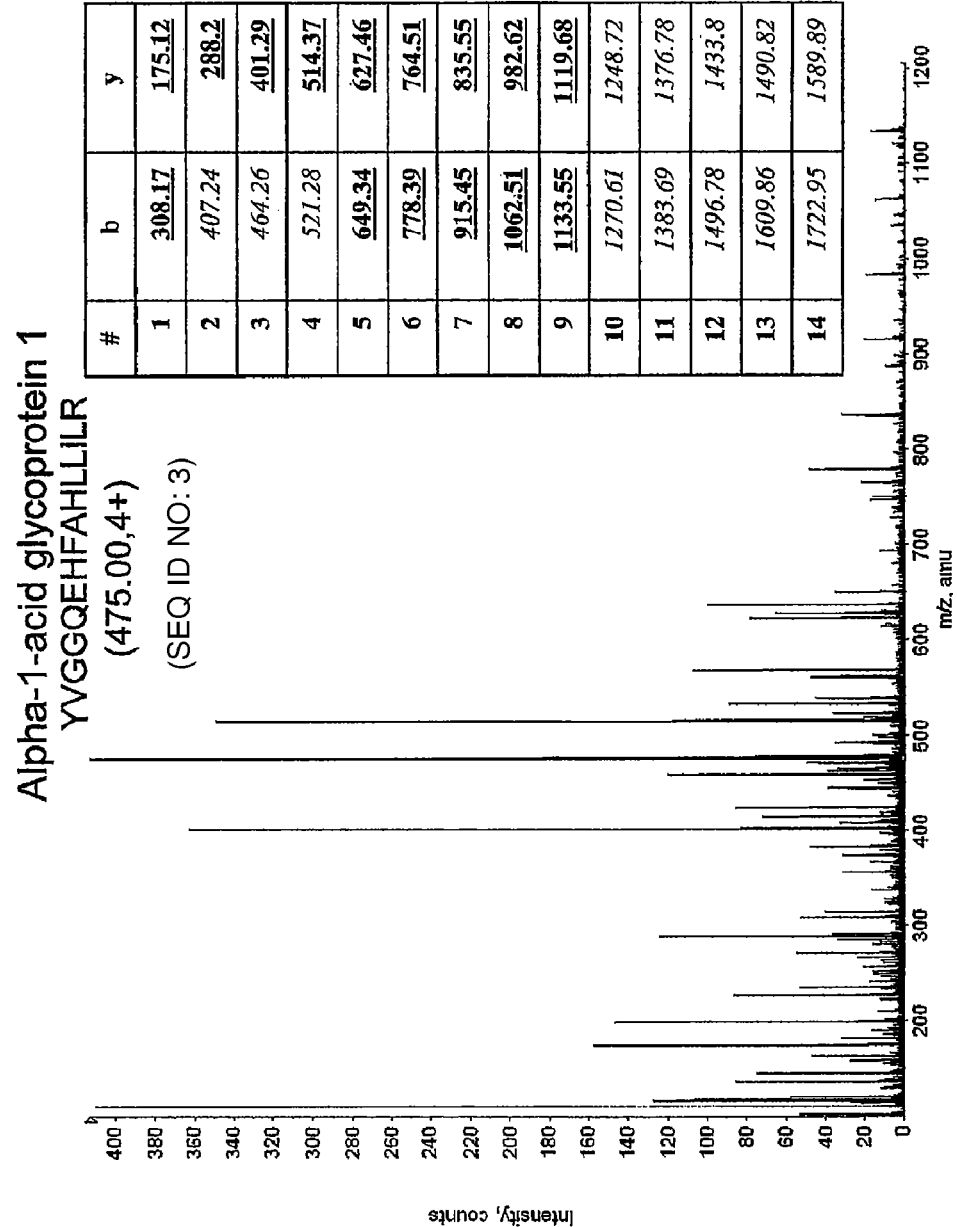
FIG. 5. (A) MS/MS spectrum of one quadruply charged peptide ion (YVGGQEHFAHLLILR (SEQ ID NO:3) at m/z=475.00 Da) originated from α-1-acid glycoprotein 1. (B) relative quantification for α-1-acid glycoprotein 1 between dry eye samples and control samples.

FIG. 3A shows MS/MS spectrum of one triply charged peptide ion, TYLISSIPLQGAFNYJ (SEQ ID NO:1) at m/z=701.10 (J represents the iTRAQ-modified lysine residue) which is originated from prolactin-inducible protein. Both b-ion series and y-ion series were observed in the mass range of 100~1200 Da. Magnified MS/MS spectrum of 111.0 to 120.0 Da gives four iTRAQ reporter ions at m/z=114.1, 115.1, 116.1 and 117.1 Da. Typically iTRAQ reagents 114 and 115 were used to label 2 control samples and iTRAQ reagents 116 and 117 were used to label 2 dry eye samples. The relative quantity of protein was based on the ratio of the peak areas of reporter ions m/z=114.1, 115.1, 116.1 and 117.1 Da. From FIG. 3B, down-regulation of prolactin-inducible protein in dry eye tears was clearly observed. FIGS. 4A and 5A show MS/MS spectra of one triply charged peptide ion (SGETEDFIADLWGLCTGQIJ (SEQ ID NO:2) at m/z=877.40 Da) originated from α-enolase and one quadruply charged peptide ion (YVGGQEHFAHLLILR (SEQ ID NO:3) at m/z=475.00 Da) originated from α-1-acid glycoprotein 1 respectively. Similarly, zoom-in MS/MS spectra (FIGS. 4B and 5B) revealed over-expression of α-enolase and α-1-acid glycoprotein 1 in dry eye tear fluid.

Example 9

ROC Curve for Dry Eye Biomarkers and Biomarker Panel

Figure 6B:
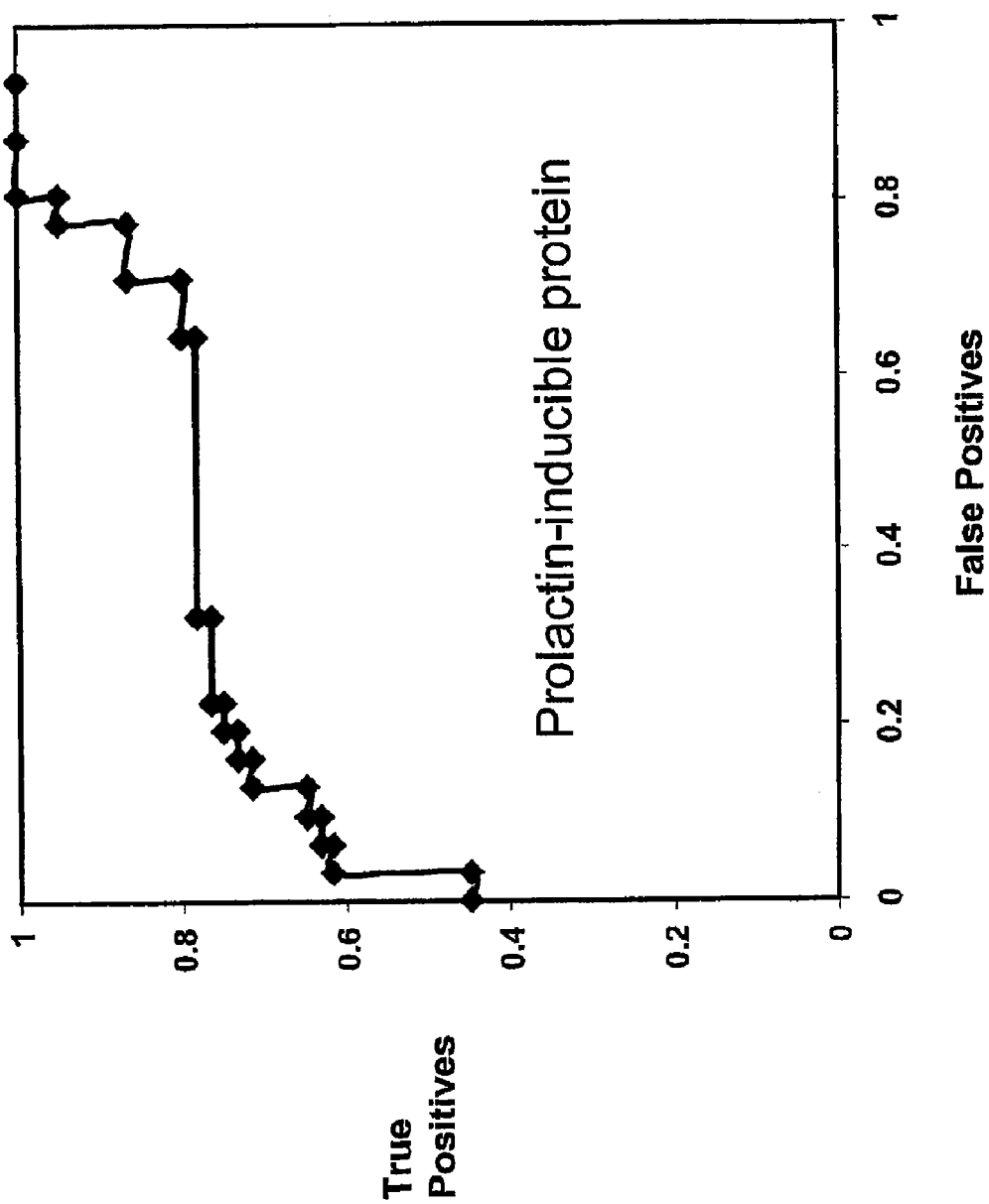
FIG. 6. (A) ROC curve when using α-enolase as the only biomarker. The accuracy (area under the ROC curve) is 85%. (B) ROC curve when using prolactin-inducible protein as the only biomarker. The accuracy (area under the ROC curve) is 81%. (C) ROC curve when using a biomarker panel. The accuracy (area under the ROC curve) is 98%.
Figure 6C:
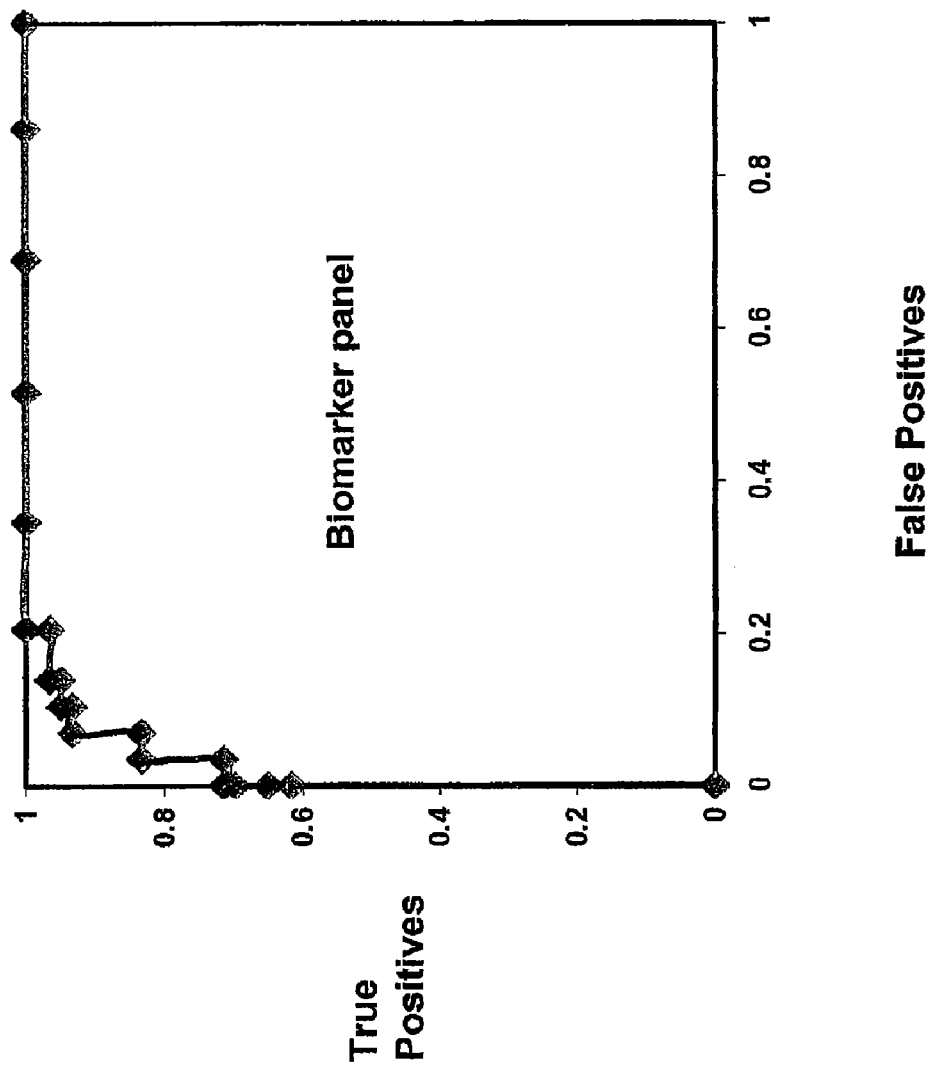

Firstly, the ROC curve was generated for each biomarker candidate individually. ROC curve plots true positive rate (sensitivity) versus false positive rate (1-specificity) of various cutoff value for DE:C ratios. The area under the ROC curve was also calculated and this area is the accuracy. The ROC curve is useful for comparing the performance of different tests. The best individual biomarker candidate among up-regulated proteins is α-enolase with the accuracy of 85% (FIG. 6A), while prolactin-inducible protein tops the down-regulated proteins with the accuracy of 81% (FIG. 6B).

Using linear classification, the best combination of biomarkers was found useful as a panel of biomarkers to profile the condition. The biomarker panel contains four proteins: α-enolase (ae), prolactin-inducible protein (PIP), von Ebner's gland protein (vEgp) and proline-rich protein 4 (pr4). The method is a two-step approach.

Firstly, a dye eye sample will be predicted if the ratio (DE:C) of α-enolase>1.70. For those samples which do not meet this criterion, the following formula will be used for further identification of dry eye cases $$y = \log 2 \text{ ratio } (pr4) - \log 2 \text{ ratio } (PIP) - 0.8 \log 2 \text{ ratio } (vEgp)$$

The cutoff value for y ranges from 0.2 to 1.8.

By using this approach, the accuracy for correctly diagnosing dry eye can be increased to 98%. It should be noted that proline-rich protein 4 has very poor performance if used as a single biomarker. However, combined with prolactin-inducible protein and Von Ebner's gland protein, proline-rich protein 4 can increase accuracy significantly.

Example 10

Potential Biomarkers which can be Used to Classify Severe, Moderate and Mild Dry Eye Based on results of one of the clinical tests, i.e. Tear breakup time (TBUT), we further classified them into three groups: severe (TBUT<2 sec.), moderate (TBUT=2~5 sec.) and mild (TBUT=5~10 sec.). Interestingly, we found only α-1-acid glycoprotein 1, S100 A8 and S100 A9 showed the trend to differentiate the severity of dry eye among the above 10 biomarkers (FIG. 7A-7D). For example, an even distribution was observed for α-enolase. However, higher levels of α-1-acid glycoprotein 1, S100 A8 and S100 A9 were associated with severity of dry eye (shorter tear breakup time).

Example 10A

Method for Providing Absolute Levels of One or More Biomarkers in Tear Samples Absolute quantitation of dry eye protein biomarker candidate in tear fluid by using iTRAQ and a synthetic peptide as the internal standard.

This constitutes an example of the approach to quantify S100 A11 protein in tear fluid from a normal, control subject and a dry eye patient. iTRAQ reagents 114 and 115 were used to label one control sample and one dry eye sample respectively, while iTRAQ reagents 116 and 117 were used to label a synthetic S100 A11 peptide fragment with the amino acid sequence (TEFLSFMNTELAAFTJ (SEQ ID NO:4)) at two known concentrations (0.5 pmol/µl and 1.25 pmol/µl). Sample preparation and 2D LC-MS/MS analysis followed the same procedures as those in Example 3 and Example 4. FIG. 8 gives the MS/MS spectrum showing the peak intensities of 114, 115, 116 and 117 which corresponded to control, dry eye and internal standard at the two different concentrations. By comparing the peak area of the reporter ions, i.e. 114, 115, 116 and 117, the absolute concentration of S100 µl protein in control tears and dry eye tears can be calculated as 10.7 ng/µg total protein and 25.4 ng/µg total protein respectively. Using this approach, we are able to do absolute quantitation of all biomarkers in one analysis by spiking known amount of different internal standards. This type of information could be used for anti-body based tests for dry eye.

Treatment

Example 11

Treatment of Dry Eye by Decreasing Expression of α-1-Glycoprotein 1

Under the present invention, the cause of dry eye due to an upregulation of α-1-glycoprotein 1 (AGP) may be treated by one or more methods to reduce or decrease any inflammation involved with AGP expression. The person skilled in the art will be able to choose a suitable anti-inflammatory treatment to reduce the expression of AGP and hence treat the condition or at least alleviate its symptoms.

Example 12

Treatment of Dry Eye Condition by Increasing Expression of Prolactin-Inducible Protein Under the present invention, the cause of dry eye due to downregulation of prolactin-inducible protein (PIP) may be treated by one or more methods to increase the expression of PIP. This may be done by the administration of prolactin and/or androgen and hence treat the condition or at least alleviate its symptoms.

Example 13

Treatment of Dry Eye Condition by Decreasing Expression of S100 A8 and S100 A9

Under the present invention, the cause of dry eye due to upregulation of S100 A8 and S100 A9 may be treated by one or more methods to reduce or decrease any inflammation involved with S100 A8 and S100 A9 production. The person skilled in the art will be able to choose a suitable treatment modality to reduce the expression of S100 A8 and S100 A9 and hence treat the condition or at least alleviate its symptoms.

Diagnostic Kit

Example 14

Diagnostic Kit for α-Enolase

A diagnostic kit for the condition of dry eye may comprise at least one chemical capable of reacting with at least one of the biomarkers of the present invention. Such as diagnostic kit may comprise a substrate for enolase such as D-glyceric acid 2-phosphate (D-GA2P) [21] or 2-phosphoglycerate (2-PG) [22] for enzymatic determination of enolase. The enzymatic reaction may also be photometrically measured in a microarray or a nanoarray [22].

It will be apparent to a person skilled in the art that the present invention may also be used in veterinary medicine for animals such as mammals.

While specific examples to practice the invention have been provided, it will be appreciated that various modifications and improvements may be made by a person skilled in the art without departing from the spirit and scope of the present invention.

REFERENCES

[1] Dogru M, Tsubota K. New Insights into the Diagnosis and Treatment of Dry Eye. The Ocular Surface; 2004; 2:59-75.
[2] Sullivan D A. Tearful Relationships? Sex, Hormones, the Lacrimal Gland, and Aqueous-Deficient Dry Eye. The Ocular Surface; 2004; 2:92-123.
[3] Schein O D, Munoz B, Tielsch J M, Bandeen-Roche K, West S. Prevalence of dry eye among the elderly. Am J Opthalmol. 1997 December; 124(6):723-8.
[4] Lemp M A. Report of the National Eye Institute/industry workshop on Clinical Trials in Dry Eyes. CLAO J. 1995 October; 21(4):221-32.
[5] Ousler G W, Gomes P J, Welch D, Abelson M B. Methodologies for the Study of Ocular Surface Disease. The Ocular Surface; 2005; 3:143-154.
[6] Ross, P. L., Huang, Y. N., Marchese, J. N., Williamson, B., Parker, K., Hattan, S., Khainovski, N., Pillai, S., Dey, S., Daniels, S., Purkayastha, S., Juhasz, P., Martin, S., Bartlet-Jones, M., He, F., Jacobson, A., and Pappin, D. J. (2004) Multiplexed protein quantitation in saccharomyces cerevisiae using amine-reactive isobaric tagging reagents. Mol Cell Proteomics 3(12), 1154-1169.
[7] Pancholi V. Multifunctional alpha-enolase: its role in diseases. Cell Mol Life Sci. 2001 June; 58(7):902-20.
[8] Hochepied T, Berger F G, Baumann H, Libert C. Alpha (1)-acid glycoprotein: an acute phase protein with inflammatory and immunomodulating properties. Cytokine Growth Factor Rev. 2003 February; 14(1):25-34.
[9] Roth J, Vogl T, Sorg C, Sunderkotter C. Phagocyte-specific S100 proteins: a novel group of proinflammatory molecules. Trends Immunol. 2003 April; 24(4): 155-8.
[10] Grus F H, Podust V N, Bruns K, Lackner K, Fu S, Dalmasso E A, Wirthlin A, Pfeiffer N. SELDI-TOF-MS ProteinChip array profiling of tears from patients with dry eye. Invest Opthalmol Vis Sci. 2005 March; 46(3):863-76.
[11] Ryan D G, Taliana L, Sun L, Wei Z G, Masur S K, Lavker R M. Involvement of S100A4 in stromal fibroblasts of the regenerating cornea. Invest Opthalmol Vis Sci. 2003 October; 44(10):4255-62.
[12] Sherbet G V, Lakshmi M S. S100A4 (MTS1) calcium binding protein in cancer growth, invasion and metastasis. Anticancer Res. 1998 July-August; 18(4A):2415-21.
[13] Kanamori T, Takakura K, Mandai M, Kariya M, Fukuhara K, Sakaguchi M, Huh N H, Saito K, Sakurai T, Fujita J, Fujii S. Increased expression of calcium-binding protein S100 in human uterine smooth muscle tumours. Mol Hum Reprod. 2004 October; 10(10):735-42. Epub 2004 Aug. 20.
[14] Ohashi Y, Ishida R, Kojima T, Goto E, Matsumoto Y, Watanabe K, Ishida N, Nakata K, Takeuchi T, Tsubota K.

Abnormal protein profiles in tears with dry eye syndrome. Am J Opthalmol. 2003 August; 136(2):291-9.

[15] Redl B. Human tear lipocalin. Biochim Biophys Acta. 2000 Oct. 18; 1482(1-2):241-8.

[16] Clark J W, Snell L, Shiu R P, Orr F W, Maitre N, Vary C P, Cole D J, Watson P H. The potential role for prolactin-inducible protein (PIP) as a marker of human breast cancer micrometastasis. Br J Cancer. 1999 November; 81(6):1002-8.

[17] Koo B S, Lee D Y, Ha H S, Kim J C, Kim C W. Comparative analysis of the tear protein expression in blepharitis patients using two-dimensional electrophoresis. J Proteome Res. 2005 May-June; 4(3):719-24.

[18] Zhou L, Beuerman R W, Foo Y H, Liu S P, Ang L P K, Tan D T H. Characterisation of human tear proteins using high-resolution mass spectrometry. Ann Acad Med Singapore 2006; 35: in press.

[19] Dickinson D P, Thiesse M. A major human lacrimal gland mRNA encodes a new proline-rich protein family member. Invest Opthalmol Vis Sci. 1995; 36:2020-2031.

[20] Thomas R. Recent developments in LC-MS-MS. Spectroscopy 16(1) 28-37 (2001)

[21] Wold F and Ballou C E. Studies on the enzyme enolase. J Biol Chem 227 (1): 301-312 (1956).

[22] Dietrich H R C et al Nanaoarrays: a method for performing enzymatic assays. Anal Chem 76:4112-4117 (2004).

The invention claimed is:

1. A method of diagnosing dry eye in a subject, the method comprising:
   (i) providing a tear fluid sample from said subject;
   (ii) measuring the expression of α-enolase in said sample by mass spectrometry; and
   (iii) comparing expression of α-enolase from said sample to a reference value from a statistically significant number of control subjects not exhibiting signs or experiencing symptoms of dry eye, wherein the subject is diagnosed with dry eye if a ratio of α-enolase from said sample to said reference value is greater than 1.70.

2. The method according to claim 1, further comprising measuring the expression of S100 A9 in said sample by mass spectrometry; and
   comparing expression of S100 A9 from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of S100 A9 from said sample to said reference value is greater than 1.20.

3. The method according to claim 1, further comprising measuring the expression of α-1-acid-glycoprotein in said sample by mass spectrometry; and comparing expression of α-1-acid-glycoprotein from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of α-1-acid-glycoprotein from said sample to said reference value is greater than 2.51.

4. The method according to claim 1, further comprising measuring the expression of prolactin-inducible protein in said sample by mass spectrometry; and comparing expression of prolactin-inducible protein from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of prolactin-inducible protein from said sample to said reference value is less than 0.66.

5. The method according to claim 1, further comprising measuring the expression of S100 A4 in said sample by mass spectrometry; and
   comparing expression of S100 A4 from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of S100 A4 from said sample to said reference value is greater than 1.50.

6. The method according to claim 1, further comprising measuring the expression of S100 A11 in said sample by mass spectrometry; and comparing expression of S100 A11 from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of S100 A11 from said sample to said reference value is greater than 1.66.

7. The method according to claim 1, further comprising measuring the expression of von Ebner's gland protein said sample by mass spectrometry; and comparing expression of von Ebner's gland protein from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of von Ebner's gland protein from said sample to said reference value is less than 0.81.

8. The method according to claim 1, further comprising measuring the expression of proline-rich 4 protein in said sample by mass spectrometry; and comparing expression of proline-rich 4 protein from said sample to a statistically significant number of control subjects not exhibiting signs or experiencing symptoms of dry eye, wherein the subject is diagnosed with dry eye if a ratio of α-enolase from said sample to said reference value is greater than 1.70 and a ratio of proline-rich 4 protein from said sample to said reference value is less than 0.912.

* * * * *

```
                         SEQUENCE LISTING

<160> NUMBER OF SEQ ID NOS: 4

<210> SEQ ID NO 1
<211> LENGTH: 16
<212> TYPE: PRT
<213> ORGANISM: artificial
<220> FEATURE:
<223> OTHER INFORMATION: synthesised
<220> FEATURE:
<221> NAME/KEY: misc_feature
<222> LOCATION: (16)..(16)
<223> OTHER INFORMATION: iTRAQ-modified lysine residue

<400> SEQUENCE: 1

Thr Tyr Leu Ile Ser Ser Ile Pro Leu Gln Gly Ala Phe Asn Tyr Xaa
1               5                   10                  15

<210> SEQ ID NO 2
<211> LENGTH: 20
<212> TYPE: PRT
<213> ORGANISM: artificial
<220> FEATURE:
<223> OTHER INFORMATION: synthesised
<220> FEATURE:
<221> NAME/KEY: misc_feature
<222> LOCATION: (20)..(20)
<223> OTHER INFORMATION: iTRAQ-modified lysine residue

<400> SEQUENCE: 2

Ser Gly Glu Thr Glu Asp Phe Ile Ala Asp Leu Trp Gly Leu Cys Thr
1               5                   10                  15

Gly Gln Ile Xaa
            20

<210> SEQ ID NO 3
<211> LENGTH: 15
<212> TYPE: PRT
<213> ORGANISM: artificial
<220> FEATURE:
<223> OTHER INFORMATION: synthesised

<400> SEQUENCE: 3

Tyr Val Gly Gly Gln Glu His Phe Ala His Leu Leu Ile Leu Arg
1               5                   10                  15

<210> SEQ ID NO 4
<211> LENGTH: 16
<212> TYPE: PRT
<213> ORGANISM: artificial
<220> FEATURE:
<223> OTHER INFORMATION: synthesised
<220> FEATURE:
<221> NAME/KEY: misc_feature
```

-continued

```
<222> LOCATION: (16)..(16)
<223> OTHER INFORMATION: iTRAQ-modified lysine residue

<400> SEQUENCE: 4

Thr Glu Phe Leu Ser Phe Met Asn Thr Glu Leu Ala Ala Phe Thr Xaa
1               5                   10                  15
```